United States Patent [19]

Saunders et al.

[11] Patent Number: 5,112,827
[45] Date of Patent: May 12, 1992

[54] DRUG TO REVERSE FATTY LIVER AND ATHEROMATOUS LESIONS

[75] Inventors: J. Palmer Saunders; Errol E. Kalmaz, both of Galveston, Tex.

[73] Assignee: Board of Regents, The University of Texas System, Austin, Tex.

[21] Appl. No.: 526,132

[22] Filed: May 18, 1990

[51] Int. Cl.$^5$ .................................. A61K 31/52
[52] U.S. Cl. ........................... 514/263; 514/824; 514/838
[58] Field of Search ............... 514/256, 838, 824, 263

[56] References Cited

U.S. PATENT DOCUMENTS 3,737,433  6/1973  Moher et al.
4,189,469  2/1980  Gleixner et al.

OTHER PUBLICATIONS

"Diagnosis and Treatment of Lower-Extremity Arteriosclerosis" Cleveland Clinic J Med 56(5): 467–468.
"Clinical Investigation of the Effects of Pentoxifylline in Patients Severe Peripheral Occlusive Vascular Disease". Curr med Res 2 Opin 9(97: 602–610).
Needleman et al (1985) Goodman and Gilman, eds., In: Pharmacological Basis of Therapeutics, 7th ed.
T. Rall (1985) Goodman and Gilman, eds., In: Pharmacological Basis of Therapeutics, Chapter 25, pp. 589–603.
Dialog Search (1990).
Granzer et al (1972) Arzeim-Forsch, 22(8): 1407–1410.
Brenner et tal (1967) Arzeim-Forsch, 17(8): 991–993.
Kuczynska et al (1988) Pol. Tyg. Lck., (Poland), 43(34): 1092–1094.
Sidorenko et al (1987) Kardiologiia, (USSR), 27(11): 77–80.
Gubski et al (1984).
Schaub et al (197) Munchener Medizinische Wochenschrift, Heft 26: 1265.
Nelemans (1972) Arzneim-Forsch (Drug Res), 220(8): 1410–1413.
Zeller et al (1966) Klin. Wschr., 44. Jahrg., Heft 17: 1022–1028.
Dettelbach et al (1985) J. Clin. Pharmacol., 25: 8–26.
Physician's Desk Reference (1989), pp. 1029–1030.
Brown et al (1985) Goodman and Gilman, eds., In: Pharmacological Basis of Therapeutics, 7th ed., pp. 827–845.

Primary Examiner—Frederick E. Waddell
Assistant Examiner—Diane Gardner
Attorney, Agent, or Firm—Arnold, White & Durkee

[57] ABSTRACT

The present invention comprises an amazingly effective method for the treatment, prevention and reversal of diet-induced high fat or alcohol-induced tissue-degernative conditions. More specifically, the present invention involves the discovery that pentoxidfylline, when administered in vivo will: (1) successfully treat diet-induced fatty liver conditions; (2) successfully treat atheromatous lesions, particularly those caused by ingestion of high levels of dietary fat and/or hypercholesterolemia; and (3) successfully treat conditions of fatty liver degeneration caused by chronic ingestion of ethanol or of toxic doses of various chlorinated hydrocarbons.

20 Claims, 11 Drawing Sheets

DRUG TO REVERSE FATTY LIVER AND ATHEROMATOUS LESIONS

Reference is specifically made herein to the Inventors Disclosure Document, filed May 7, 1990, #252439.

BACKGROUND OF THE INVENTION

1. Field of the Invention

The present invention relates to therapeutic methods for the treatment of fatty tissue deposits and alcohol-related liver degeneration. More particularly, the present invention relates to the treatment of these conditions using a particular group of compounds, the dimethylxanthines, and bioactive-equivalent derivatives thereof. The present invention also relates to compounds which alter lipid metabolism, and which possess therapeutic value in the treatment, prevention and reversal of liver degeneration and fatty tissue deposits.

The present invention also relates to therapeutic methods for reducing and/or reversing atheromatous lesions. The present invention also relates to therapeutic methods effective in the treatment, prevention and reversal of cirrhosis of the liver.

2. Description of the Related Art

Medical science has recognized a number of diet induced pathological changes in humans which result from excess alcohol or fat (i.e., cholesterol) ingestion. High cholesterol diets have been associated with disease of the large arteries, such as cardio-vascular disease. Complications of cardiovascular disease are the major cause of death in most industrialized countries, and atherosclerosis is the primary process associated with this high mortality. This disease of the large arteries has increased markedly over the past decade, making the creation of methods for its prevention and treatment a critical challenge to the medical community. The American Heart Association reports that approximately 65 million Americans suffer from serious vascular disease, while alcoholism, with its concomitant syndromes of fatty liver disease and cirrhosis, evidencing an equally grim frequency.

The epidemic proportion of reported cases of serious vascular (i.e. cardiovascular) disease and liver disease related to high-cholesterol and/or alcohol intake has raised general public awareness of these conditions and measures which may be taken to attempt their control.

Chronic ingestion of ethanol or of toxic doses of various chlorinated hydrocarbons are known to cause liver degeneration (fatty liver) and cirrhosis in man[3,5] and in experimental animals[1-3]. These and related conditions caused by chronic alcohol consumption cause a reported 10 million cases of advanced alcoholism disease in the United States alone. Associated with chronic alcoholism is excessive mobilization of lipids and the ultimate development of a fatty liver.

The mechanism of production of fatty hepatosis is not entirely clear, but appears to be a combination of several factors, such as sparing action of ethanol oxidation on utilization of liver triacylglycerols, excessive mobilization of triacylglycerols from adipose tissue to the liver caused in part by action of ethanol in triggering release of hormones, and failure to synthesize sufficient lipoprotein for transport of triacylglycerols because of alterations of amino acid availability.

The condition of cirrhosis of the liver relates to a group of chronic diseases of the liver characterized pathologically by the loss of the normal microscopic hepatic lobular architecture, with fibrosis and by destruction of parenchymal cells and their regeneration to from nodules. The disease has a lengthy latent period, usually followed by the sudden appearance of abdominal swelling and pain, hematemisis, dependent edema, or jaundice.

Fatty cirrhosis, more particularly, is characterized by the type of cirrhosis in which liver cells are infiltrated with fat (triglycerides), the infiltration usually being due to alcohol ingestion.

Currently, cirrhosis has been clinically managed through the treatment of the symptoms associated with it. However, methods of reversing or preventing the damage associated with I5 such dietary-induced liver damage have not as yet been available. These conditions are not generally cleared by the administration of choline.

Another dietary-related malady resultant from abnormal lipid mobilization and deposition is dietary hypocholesterolemia. High cholesterol diets (high concentrations of dietary carbohydrate or triacylglycerol) in animals have been shown to result in the formation of fatty deposits at multiple tissue sites, particularly on the heart, liver and large arteries.

Methods of treating these conditions are relatively non-existent, while any method for providing the regeneration of damaged liver tissue is at this time unknown.

The condition of hypercholesterolemia has been primarily observed in persons consuming high cholesterol-containing diets or diets which include high ethanol concentrations. The predominant lipid fraction in an ethanol compromised liver is triglyceride[1-5]. However, significant increases in the levels of cholesterol esters and cholesterol[1-7], phospholipids[2-6], and lipoproteins have been reported[7].

Although a high fat diet accentuates fatty infiltration of the liver[8], endogenous biosynthesis of fatty acids is the main cause of hepatic steatosis in chronic alcoholism[2,9,10]. This alteration is further aggravated by impaired oxidation of fatty acids in an ethanol compromised liver[11]. The explanation for the ethanol induced increase in hepatic deposition of fat is still not very well understood. However, most investigators believe that ethanol inhibits hepatic fatty aoid oxidation which secondarily causes fatty acids to be stored as triacylglycerol.

Recent studies of Kosenko and Kaminsky[12] demonstrated that ethanol consumption decreases the [NADP]/[NADPH] ratio in non-fasted rats, and both ethanol withdrawal and fasting in ethanol ingesting animals appears to increase the ratio to normal or higher levels. Ethanol has also been shown to decrease total hepatic [NAPD]/[NADPH] ratio upon chronic ingestion in the rat[13]. In other studies on the hepatic redox state, ethanol was reported to decrease the free cytosolic and mitochondrial [NAD]/[NADH] ratios[14,15].

Fatty liver as a concomitant of the ingestion of high fat diets, alcohols or chlorinated hydrocarbons is a well-known phenomenon. Chronic intake of ethanol results in, among other things, hepatic injury to the accumulation of triglycerides and eventually, cirrhosis. Acute alcohol ingestion in man has not clearly been associated with alteration of hepatic function; however, in chronic ethanol ingestion as well as ethanol withdrawal are factors affecting the activities of NADPH-generating enzymes and their quantitative contribution to an ADPH-generation in liver. Furthermore, the variation of hepatic [NAD]/[NADH] ratio occurs in ethanol treated rats, which is a function of both ethanol dose and time following its administration[16]. It has been suggested that the elevated concentration of NADH creates conditions favoring increased lipid synthesis and that the latter contributes to the development of fatty livers in chronic alcoholics[17,18].

A triglyceride concentration in the range of 200–800 mg/dl with a normal or near normal cholesterol concentration almost always indicates a simple elevation of VLDL. Triglyceride concentrations greater than 1,000 mg/dl usually indicate the presence of chylomicrons, either alone or in addition to elevated VLDL. Circulating LDL constitutes the major reservoir of cholesterol in human plasma, accounting for 60 to 70% of the total. When liver or extrahepatic tissues require cholesterol for the synthesis of new membranes, steroid hormones, or bile acids, they synthesize LDL receptors and obtain cholesterol by the receptor-mediated endocytosis of LDL. Conversely, when tissues no longer require cholesterol for cell growth or metabolic purposes, they decrease the synthesis of LDL receptors.

In addition to degradation by specific receptors, lipoproteins are also disposed of by less specific pathways, some of which operate in macrophages and other scavenger cells. When the concentration of lipoprotein in plasma rises, the rate of its degradation by such pathways increases. This contributes to the deposition of cholesterol in such abnormal locations as arterial walls (producing atheromas) and of macrophages in the tendons and skin (producing xanthomas)[19].

A diet with reduced cholesterol and fat are effective in the clinical management of some forms of high-blood lipid conditions. For example, Anitschow demonstrated that some regression of cholesterol-diet induced atherosclerotic lesions were evidenced by the maintenance of animals on a normal diet for periods ranging from 18 to 24 months[27].

Other studies have shown that r®duction of dietary-induced lesions after restoration of normal diets in rabbits (and other animals) could be accelerated and markedly enhanced when the normal regimen is supplemented by feeding chelating agents[27], by production of hyperoxemia[28], by combination of cholestyramine and hyperoxemia[29], by a combination of diphosphonate and colchicine[30], and by clofibrate[31].

An important feature in the development of atherosclerotic lesions is the injury to the endothelium and the change in endothelial permeability to various blood materials. Materials contained in the blood subsequently pass through those compromised endothelial tissues and into the intima of the arterial wall. It has been demonstrated that even a moderate increase in endothelial permeability is accompanied by a significant increase in the incidence of atherosclerotic events[26].

Despite the intense work in this area of medical research, atherosclerotic disease, such as arteriosclerosis, remains a significant medical problem. The high incidence of diets rich in fat exacerbate even the mildest of artherosclerotic conditions over time. Secondary physiological effects, which often accompany the onset of such atherosclerotic maladies, include sub-optimal liver function. Unfortunately, diet induced liver disease is clinically treated as irreversible tissue damage.

Diet is not always effective in the management of all or most forms of hypercholesterolemia or hypertriglycemia. Many therapeutic agents currently on the market have been used where diet is ineffective to control abnormally high blood lipid levels, as well as the secondary maladies high blood lipid concentrations cause.

Abundant circumstantial evidence indicates that treatment of hyperlipoproteinemia will diminish or prevent atherosclerotic complications. As a result, several pharmaceutical agents have been developed to treat these conditions. The most widely known of these agents include nicotinic acid (a particular methylxanthine compound), Ronitol (which has an alcohol which corresponds to nicotinic acid), clofibrate (atromid-S), Gemfibrozin (for treatment of hyperlipoproteinemia, a structural congener of clofibrate), compactin and mevinolin (HMG CoA reductase inhibitors - are fungal metabolites), Choloxin®, (i.e., dextrothyroxine -( sodium), Neomycin (oral administration only hypolipidemic effect - reduces LDL), beta-sitosterol (a plant sterol -lowers LDL, not VLDL), and probucol (4,4'-(isopropylidenedithiol)-bis(2,6-di-t-butylphenol)[20].

Nicotinic acid was discovered as a hypolipidemic drug in 1955[21]. Specifically, nicotinic acid acts to reduce elevated concentrations of VLDL and its daughter particles, LDL and IDL. While pharmacological doses of nicotinic acid are useful in the treatment of most forms of hyperlipoproteinemia, such is limited by the frequent occurrence of a constellation of side effects. The side-effects normally attendant such use include intense cutaneous flush, pruritus increased arterial fibrillation, gastrointestinal irritation, hepatotoxicity, and other cardiac arrhythmias.

Additionally, the side effects associated with nicotinic acid results in poor patient compliance with prescribed doses. Beneficial effects reported from prolonged nicotinic acid administration include the regression of eruptive, tuboeruptive, tuberous and tendon xanthomas. Niacin (nicotinic acid) is contraindicated in patients when hepatic dysfunction, which is an almost certain concomitant of hypercholesterolemia. Consequently, nicatinic acid is contraindicated in those patients with hepatic dysfunction.

While nicotinic acid does not produce any detectable changes in total body synthesis of cholesterol it significantly alters the excretion of bile acids in man[22]. Additionally, it is known to inhibit lipolysis in adipose tissue, decrease esterification of triglycerides in the liver, and to increase the activity of lipoprctein lipase[23].

Clofibrate has been described as the one of a series of aryloxyisobutyric acids which are effective in reducing plasma concentrations of total lipid cholesterol with minimal toxicity However, questions recently have arise as to its actual effectiveness[24]. This, together with its now recognized latent adverse effects, have circumscribed its use to almost exclusively the treatment of familial dysbetalipoproteinemia (type-III hyperlipoproteinemia). It has also occasionally been useful in patients with severe hypertriglyceridemia as a last resort in patients who do not respond to nicotinic acid or gemfibrozil. Chemically, clofibrate is the ethyl ester of p-chlorophenoxyisobutyric acid.

In the treatment of familial dysbetalipoproteinemia, the use of clofibrate results in a significant reduction of cholesterol and mobilization of deposits of cholesterol in tissues, accompanied by regression and disappearance of xanthomas. Clofibrate has no effect on hyperchylomicronemia, nor does it affect concentrations of HDL (except in some hypertrigiyceridemic subjects in whom marked reduction of VLDL may be accompanied by modest increments in HDL)[20]. Side effects associated with clofibrate include nausea, diarrhea, weight gain, skin rash, alopecia, impotence and a flu-like syndrome. The flu-like syndrome, where it does occur, is also associated with severe muscle cramps and tenderness, stiffness and weakness. Cholelithiasis and cholecystitis have also been associated with this drug by the enhancement of particular enzymes.

Clofibrate is contraindicated for patients with cardiac artery disease, owing to the risk of drug-induced cardiac arrhythmia, cardiomegaly, increased angina, claudication and thromboembolic pneumonia[20].

Gemfibrozil has been used for the treatment of hyperlipoproteinemia, and is a structural congener of clofibrate. It has been shown to be effective in reducing the plasma concentration of VLDL in hypertriglyceridemic patients who do not respond to diet. Gemfibrozil has also been shown to raise plasma concentrations of HDL. The drug has shown only limited ability to reduce LDL, as plasma LDL-cholesterol has been reported as reduced by less than 10% in hypercholesterolemic patients[20]. However, clinical evidence of this drug is limited, and its long-term safety has yet to be established.

Gemfibrozil has been shown to inhibit lipolysis of stored triglyceride in adipose tissue and to decrease the uptake of fatty acid by the liver[25]. Side effects associated with its use include gastrointestinal distress, abdominal pain, diarrhea, nausea, eosinophilia, skin rash, mucoskeletal pain, blurred vision, mild anemia, leukopenia, and the enhancement of gallstones.

Probucol has been demonstrated to cause a: moderate reduction in plasma concentrations of LDL-cholesterol. Probucol has several properties that set it apart from other lipid-lowering drugs. Two of these properties may limit its clinical utility. For example, it is a highly hydrophobic compound, and it thus persists in adipose tissue for months after patients stop taking it. Additionally, it has been shown to cause a substantial lowering of plasma HDL-cholesterol concentrations in addition to its effects on LDL[20]. Long-term effects of the drug are not yet known.

Probucol has no apparent structural similarity to other agents that lower cholesterol concentrations. It is a sulfur-containing bis-phenol. The known effects on plasma concentrations of VLDL and triglycerides are minimal. Side effects of this drug include diarrhea, flatulence, abdominal pain, and nausea[20]. Fatal cardiac arrhythmias have also been shown in experimental animals that have received a diet high in cholesterol and saturated fat. It is medically advised that probucol be reserved for the treatment of hypercholesterolemia in patients with excessive plasma LDL concentrations who cannot be controlled with dietary management and more conventional drugs. Additionally, because of its potentially undesirable effect in lowering HDL concentrations, probucol is not widely recommended, and is not known to benefit patients with hypertriglyceridemia. There is, as yet, no evaluation of the efficiency of probucol for the prevention or control of atherosclerosis or its clinical sequela.

Cholestryamine is a chloride salt of a basic anion-exchange resin. Cholestipol hydrochloride is a second of these bile-acid binding resins which is a copolymer of dimethyl pentamine and epichlorohydrin[20]. These bile-acid binding resins characteristically reduce the concentration of cholesterol in plasma by lowering the level of LDL, usually to about 20%. In most patients, reported concentrations of triglyceride in plasma (VLDL) increase by 5 to 20% initially and then returns to normal. Body pools of chclesterol are reportedly decreased after long-term therapy with bile acid-binding resins, and there has been some regression of xanthomas reported[20].

Side effects of these drugs include nausea, abdominal discomfort, indigestion, constipation, and impaction.

Compactin and mevinolin are two M/HMG and CoA reductase inhibitors which chemically differ from each other only by one methyl group. They both resemble HMG CoA, the natural substrate of HMG CoA reductase. Mevinolin is currently under study in the United States as an investigational drug. It is medically recommended that until the long-term safety of mevinolin and compactin is established, use of these drugs should be reserved for the experimental treatment of patients with the heterozygous form of familial hypercholesterolemia. These agents are not useful for the treatment of hypertriglyceridemia.

Choloxin (dextrothyroxine sodium) is the original isomer of the hormone, L-thyroxine. Plasma concentrations of VLDL and HDL are not changed significantly. Side effects associated with this drug include an increase in frequency or severity of anginal attacks in patients with coronary heart disease, cardiac arrhythmias, nervousness, sweating, tremor and insomnia. The use of this drug is medically recommended to be restricted to young patients with familial hypercholesterolemia or polygenic hypercholesterolemia, who are known to be free of coronary artery disease and who do not respond to diet and more conventional drugs.

It is clear that extensive research and interest in the treatment of those physiological conditions precipitated from high dietary fat and cholesterol ingestion (postulated to precipitate atheromatous lesions, fatty deposits, and more specifically, fatty cirrhosis of the liver) exists. However, there remains to be elucidated more effective methods for reducing circulating lipids without the multiple side effects of conventional blood lipid-reducing drugs. Additionally, a method is still needed which would both treat and reverse the tissue damage associated with such lipid deposits. The development of a method which would actually regenerate lipid and alcohol-related tissue damage, such as those attendant cirrhosis of the liver, would provide a major advancement in the clinical management of patients with diet-compromised liver function and morphology.

Pentoxifylline is a methylxanthine which is an FDA approved pharmaceutical agent. It has been used as a peripheral vasodilator in the treatment of intermittent claudication[32]. Several derivatives of theobromine have also been synthesized and tested for potential use in the treatment of peripheral vascular and cardiopulmonary diseases. A water-soluble derivative of theobromine similar to pentoxifylline, [1-$\beta$-hydroxypropyl substitution instead of 1-5- oxo hexyl substitution], has been shown to be an effective bronchodilator when administered by aerosol inhalation[33]. However, the systemic vascular effects of this hydroxypropyl derivative have not yet been examined.

Pentoxifylline has the following chemical name: 1-[5-oxohexyl]-3,1-methylxanthine. Its structural similarities to the methylxanthine contained in beverages are as follows: triple 1,3,7 substitution like caffeine; 3,7-dimethyl substitution similar to theobromine and in contrast with 1,3-dimethyl substitution of theophylline. As a pharmaceutical agent, PTX has been prepared in a mixture with a saliva forming agent[34] to enhance the agent's biocompatibility with the gastrointestinal tract of a patient.

Pentoxifylline has been demonstrated to have particular cardiac effects, such as enhanced cardiac output[35]. However, clinical studies supporting the efficacy of orally administered pentoxifylline show no effect on heart rate, blood pressure and cardiac output. The effect of pentoxifylline is not active or musculotropic vasodilation, in contrast with the effect of the methylxanthine, aminophylline.

Most patients followed in pentoxifylline clinical studies were also suffering from non-diabetic forms of arteriosclerosis obliterans, Buerger's disease or varicose veins, and were clinically evaluated after intravenous, intramuscular or intra-arterial injections of pentoxifylline. The initial observations following the intravenous injection of pentoxifylline suggested an improvement of blood flow to ischemic limbs in patients with intermittent claudication.

An increase in microcirculation of ischemic leg tissue is described as resulting from pentoxifylline-induced alterations in flow properties of the blood in general, and of erythrocytes in particular. This effect also results in an improvement in oxygen supply to the muscles. Ehrly and colleagues have explained the improvement in oxygen supply to the muscles as a result of improved erythrocyte flexibility and increase in microcirculation[36]. Overwhelming evidence supports the proposition that improvement in capillary blood flow is brought about by increasing erythrocyte flexibility, both of which are reduced in patients suffering from intermittent claudication.

Another significant effect of pentoxifylline treatment is a reduction in plasma fibrinogen level. A reduction in plasma fibrinogen level may reduce blood viscosity severely enough to cause bleeding reactions. It is not yet possible to define the importance of improved red cell flexibility relative to that of reduced plasma fibrinogen level in effecting a reduction in whole blood viscosity.

Other effects of PTX have been shown to include the reduction of antiplasmin activity[37] elevation of plasminogen concentration[38] inhibition of platelet aggregation[39] enhancement of fibrinolytic activity[40] stimulation of prostacyline production in the endothelial cells of the vessel wall[41] and elevation of platelet CAMP concentration[42].

Complications of cardiovascular disease are the major cause of death in most industrial countries, with atherosclerosis being the primary physiological process associated with this mortality[43]. A method for reducing and reversing lipid deposition believed to precipitate the tissue damage (e.g. xanthomas lesionary), without patient-deterring side effects would present a substantial advancement in the treatment of an ever growing health problem.

The development of a method using currently acceptable pharmaceutical agents for the treatment of these fat, alcohol, and other diet-related maladies would present a significant step in the rehabilitation and cure of these and other high lipid and/or ethanol diet-induced conditions.

SUMMARY OF THE INVENTION

The present invention relates to the surprising discovery of an effective method for clearing fatty liver conditions and the like. Even more generally, the described methods are shown to be effective in the general reversal of fatty deposit conditions, such as atheromatous and arteriosclerotic lesions. This specific effect has been found through the use of particular dimethylxanthine compounds. The dimethylxanthines expected to be effective for the disclosed methods include any compound of which pentoxifylline itself is a metabolite as well as any dimethylxanthine which has a bioequivalent activity of pentoxifylline as described herein. More specifically, dimethylxanthines, such as pentoxifylline (1-[5-oxohexy1]-3,7-methylxanthine), have surprisingly been found to reverse fatty and cirrhotic liver conditions and to reverse atheromatous lesions.

The present invention presents the surprising and unexpected therapeutic use of pentoxifylline for the treatment, prevention and actual reversal of those conditions associated with high dietary fat or alcohol consumption. More specifically, pentoxifylline has been discovered to actually reverse atheromatous lesions of liver and heart tissue and to allow the regeneration of non-diseased tissues therefrom. This compound has been found to be effective in clearing fatty liver and in reversing atheromatous lesions in diet-induced hypercholesterolemic animals.

The effect of a particular dimethylxanthine, pentoxifylline, has been found to be significantly greater than theophylline. In contrast, theophylline was characterized in the past as having the most potent bioactivity of the dimethylxanthines, as determined by its effect on a variety of measurable physiological parameters. While the ability of pentoxifylline to stimulate lipolysis has been demonstrated experimentally to be greater in the presence of adrenalin than the level of lipolysis observed with theophylline and adrenalin, such failed to appreciate the activity of pentoxifylline used alone as a therapeutic agent, particularly for the methods described herein.

In actual in vivo studies, Applicants were able to show an overall reduction in fat content in liver specimens obtained from treated animals maintained on a high cholesterol-containing diet. Other observations in pentoxifylline-treated animals included a significant change in the distribution of smooth muscle cells in the arterial wall and a reduction in the quantity of foamy giant cells in the intima. These observed changes occurred in animals which were severely ill with arterial disintegration and probable fatally fat-engorged livers, making it apparent that a truly exciting phenomena was being observed by the Applicant.

Implementing the above surprising and unexpected interactions of pentoxifylline with lipid accumulation, deposition and destruction of tissue, the present invention includes a method for reversing fatty liver. Specifically, this method comprises first identifying a patient having fatty liver, administering to that diseased patient a fatty deposit-reversing concentration of pentoxifylline, and continuing administration of pentoxifylline until a reversal of the fatty liver is manifest in the diseased patient.

Reversal of the fatty liver condition is detectable by the observation of a reduced concentration of toxins in the blood from pre-treatment levels. For example, blood tests for conjugated bilirubin and serum transaminase, both of which are markedly elevated in patients with the severe liver pathology described, would exhibit a return to normal levels if the fatty liver condition were reversed or improved.

More specifically, conjugated bilirubin levels of above a normal ranqe of 0.3 to 1.0 mg/dl would be indicative of liver disease, with post-treatment conjugated bilirubin levels of about 0.3 to 1.1 mg/dl being indicative of an improvement of or a reversal of a diseased liver state. Where serum transaminase is the particular blood marker being followed, serum levels of above about 15–40 units aspartate amino-transferase (e.g., 50–300 units) is considered to be indicative of a diseased liver condition. Thus, post-treatment serum transaminase levels of about 15–40 units aspartate amino transferase would be indicative of an improvement of or a reversal of a diseased liver condition. Abnormally high levels of serum transaminase have been recognized in patients with liver dysfunction of 50–300 units aspartate amino transferase.

Methods for measuring serum conjugated bilirubin levels are well known to those of skill in the art.[54, 55, 56] General reference articles by Arvan et al., Cavallo et al. and Scharschmidt et al., which describe and/or relate to measurement of conjugated bilirubin are specifically incorporated herein by reference for this purpose. Methods for measuring transaminase levels are similarly well known to those of skill in the art.[57, 58] The Porikos et al. and Ottmar et al. references, which describe or relate to the measurement of serum transaminase, are specifically incorporated herein by reference for this purpose.

Other physiological indications of a diseased liver condition include variable increases in alkaline phosphatase activity (normal values being about 2 units), possible hypokalemia (normal values being about 3.5–5.0 mEg/l), possible hyperuricemia (due to depressed urinary excretion of uric acid), and acute severe hemolysis (associated with hyperlipemia). Hypokalemia is usually due to increased urinary excretion of potassium, and results in levels of between 3.5–5.0 mEG/l.

Additionally, the improvement or reversal of a fatty liver condition could be detected by physical examination. For example, physical examination by palpitation to reveal an enlarged, firm and tender liver is evidence of a diseased liver condition, an improvement in which would be evidence of an improvement or reversal of a diseased liver condition. Pronounced abdominal distention with ascites and jaundice is another manifestation of liver disease, with a decrease or cessation of such a condition being evidence of an improvement of or a reversal of liver disease.

In a most preferred application of this method, the fatty liver condition is further defined as cirrhosis of the liver. These conditions normally arise in patients who ingest high amounts of ethanol (alcohol) or toxic concentrations of chlorinated hydrocarbons.

In another particularly preferred embodiment of the invention, a method for reversing atheromatous lesions is described. While the reversal of such lesions at any body site is believed to be effected with the described method, the highest use to which the described method is to be used is in the treatment of those lesions which occur on the heart or liver tissues.

Insofar as the present invention is effective for the reversal of atheromatous lesions, the present invention also comprises an effective method for treating arteriosclerosis.

In that pentoxifylline has been found to reduce and regenerate the conditions precipitous of a high cholesterol-containing diet, the invention also comprises a method of reducing blood lipid levels. For this particular use, the present invention in a particularly preferred embodiment comprises a method for reducing circulating blood lipids in an animal comprising administering to an animal a lipid-reducing concentration of pentoxifylline. Most preferably, the pentoxifylline or a derivative thereof with bioactive equivalency, is to be administered daily for a period of at least 35 days. The most preferred mode of administration is oral in the form of tablets or capsules. For human use, it is postulated that a regimen of three 400 mg tablets per day will effectively reduce blood lipid levels and reverse atheromatous lesions.

It is expected that the described treatment regimen will serve to regenerate the cirrhotic nodular degenerated tissue of a fatty liver condition. The optimal dose of pentoxifylline, or bioactive derivatives thereof, to be used will of course vary depending upon the age, weight, and sex, as well as any other medications being taken by the particular patient or the existence of any complicating significant medical conditions of the patient being treated.

While any bioactive equivalent of pentoxifylline or compound which includes pentoxifylline as a metabolite are expected to be effective for the described methods and uses, the most preferred embodiment of the compound is defined as comprising the following chemical structure:

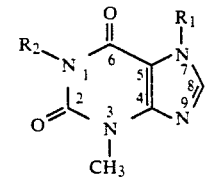

Additional chemical structural-activity studies are proposed by the inventors to further define the existence of any structural dependence of the bioactive species useful for described therapeutic methods.

$R_1$ in the above molecule is hydrogen or methyl.

$R_2$ in the above molecule is hydrogen, an alkyl group having between 1 and 10 carbon atoms, or a ketone, wherein $R_2$ is not hydrogen when $R_1$ is hydrogen. Most preferably, $R_1$ is methyl and $R_2$ is a ketone. In an even more preferred embodiment of the invention, $R_2$ is the particular ketone, 5-hexone, wherein the keto group extends from the fifth carbon of a six carbon chain.

The most preferred compound for use in the described method comprises pentoxifylline. Pentoxifylline has the following chemical structure:

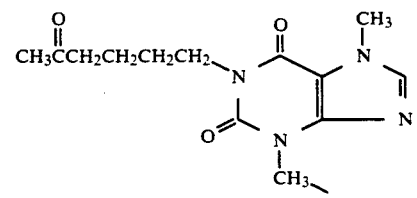

Any dimethylxanthine derivative having the equivalent bioactive effects demonstrated by pentoxifylline in reducing lipid accumulation and deposit, or reversing the tissue damage resultant of such lipid fatty deposits or accumulation, would be included in the description of those compounds useful in the present inventive methods.

The following abbreviations are used throughout the Specification:
PTX = pentoxifylline
mg = milligram
μm = micrometer
M = molar
mg = milligram
g = gram
mM = millimolar
μl = microliter
kg = kilogram
bw = body weight
vol/vol = volume to volume

DETAILED DESCRIPTION OF THE PREFERRED EMBODIMENTS

Figure 1:
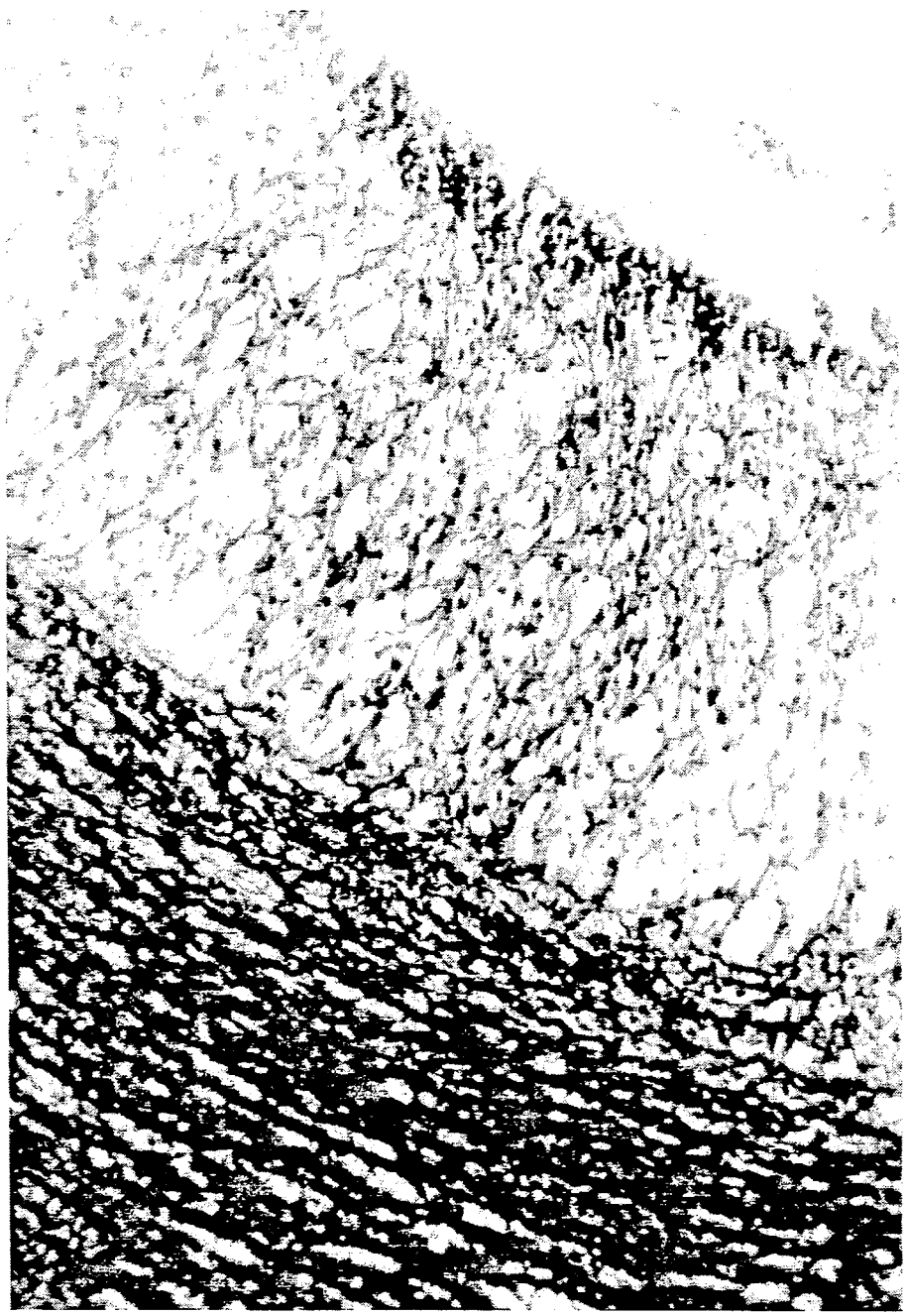
FIG. 1. This section is taken from the thoracic aorta of an untreated cholesterol-fed rabbit (fed 2% cholesterol enriched diet for 9 weeks thereafter cholesterol diet substituted with standard rabbit chow for additional 9 weeks). There is a marked proliferation of giant smooth muscle cells of the aorta and appearance of large quantity of foam cells in the intima. This section also shows substantially thickening of the intima, sporadic formation of subendothelial zone where endothelial cells have disappeared. Hematoxylin Eosin stain, 50X).

Increasing interest in the interaction of pentoxifylline with various aspects of leukocyte function, as well as its recently reported inhibition of inflammatory reactions, has created an enormous interest in pentoxifylline and related compounds. Pentoxifylline was previously thought to affect only the rheological properties of red blood cells. Pentoxifylline is also known to reduce blood viscosity by virtue of its effect on erythrocyte flexibility. However, the present invention encompasses the heretofore unknown therapeutic value of pentoxifylline in the treatment and reversal of diet-induced tissue damage.

Pentoxifylline is a compound currently approved for human use. Pentoxifylline used in the present study was obtained from Hoechst-Roussel Pharmaceutical. This drug has until this time been used only for the treatment of chronic occlusive arterial disease.

Applicants in the present disclosure describe a particular group of methylxanthine derivatives, especially dimethylxanthines such as pentoxifylline, which are valuable in the treatment of diet-induced fatty liver or arterial fatty deposits. Pentoxifylline is a representative methylxanthine of the group of compounds Applicants consider potentially effective for the described therapeutic uses. Any of the particularly defined methylxanthines of the present disclosure which exhibit properties similar to those of pentoxifylline are considered compositions potentially effective in the practice of the present invention.

The methylxanthines effective for the disclosed uses include any substance of which pentoxifylline itself is a metabolite. Other methylxanthines with different substituent groups on the xanthine molecule would be expected to exhibit similar properties. The methylxanthine molecule with the particularly defined "R" groups displayed below embody those compounds believed to be effective for the described inventive uses and methods:

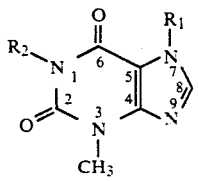

Referring now to the displayed methylxanthine nucleus having a methyl group at the #3 position, the structure of those compounds contemplated to have bioactivity effective for the described methods further includes two "R" groups. These two "R" groups are designated $R_1$ and $R_2$ in the model. In a preferred embodiment, $R_1$ is either hydrogen or methyl. $R_2$ is preferably hydrogen, an alkyl group having between 1 and 10 carbon atoms or a ketone. In a most particularly preferred embodiment of the claimed therapeutic methods, the methylxanthine compound is further defined as comprising the displayed methylxanthine nucleus wherein $R_1$ is either hydrogen or methyl and $R_2$ is hydrogen, an alkyl group having between 1 and 10 carbon atoms or a ketone, and wherein $R_2$ is not hydrogen when $R_1$ is hydrogen.

Particular examples of pharmaceutical agents useful for the claimed methods, and which are included within the chemical structures defined, include by way of example: theobromine (3,7 dimethylxanthine) ($R_1$=methyl, $R_2$=hydrogen); caffeine (1,3,7 trimethylxanthine), $R_1$=methyl, $R_2$=methyl); theophylline ($R_1$=hydrogen and $R_2$=methyl); and pentoxifylline ($R_1$=methyl; $R_2$=5 hexone).

Compounds of which these chemicals are themselves metabolites are also contemplated as capable of effecting the described therapeutic uses and methods.

In a particularly preferred embodiment, $R_2$ is a ketone. The keto group of said ketone is most preferably separated from the xanthine nucleus by a chain of 2 to 6 carbon atoms. In a particularly preferred embodiment, the keto group of said ketone is further defined as being separated from the xanthine ring by a carbon chain of 4 carbon atoms, with the keto group extending from a fifth carbon atom. Most preferably, the keto group is part of a six carbon chain.

$R_1$ in this particularly preferred embodiment is methyl. In this particular most preferred embodiment of the pharmaceutical agent, wherein $R_1$ is methyl and $R_2$ is a ketone in which the keto group is separated from the xanthine nucleus by 4 carbon atoms, the methylxanthine is pentoxifylline. Thus, the most particularly preferred embodiment of the defined agent is known as pentoxifylline. $R^2$ is most preferably defined as comprising a ketone, wherein the keto group extends from the fifth carbon atom from the xanthine nucleus, in a six carbon chain. The keto group thus extends from the fifth carbon atom of a 6 carbon chain. More specifically, $R^2$ in this most particularly preferred embodiment of the invention is 5-hexone. This compound, wherein $R^1$ is methyl and $R^2$ is 5-hexone is pentoxyfylline. Pentoxifylline has the following chemical structure:

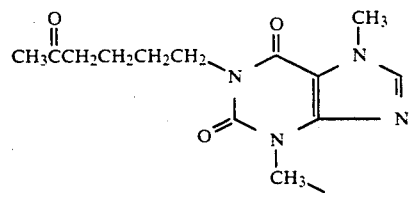

The described methylxanthine derivatives, and especially those with a ketone side chain, for example, pentoxifylline, are discovered to be effective to reverse, treat and prevent conditions of fatty liver and atheromatous lesions and their related conditions. Additionally, bioactive equivalent methylxanthine derivatives of pentoxifylline, and the methylxanthines described in the $R_1$ and $R_2$-substituted methylxanthine structure, are also expected to be capable of effecting the claimed therapeutic methods and treatments.

In that present invention is effective in the treatment of atherosclerosis, the present invention also comprises a method for treating arteriosclerosis comprising: identifying a patient having arteriosclerosis; administering to the identified patient an arteriosclerotic-reversing regimen of a methylxanthine compound having the formula:

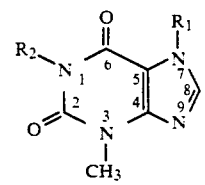

wherein $R_1$ is hydrogen or methyl and wherein $R_2$ is hydrogen, a ketone or an alkyl having between 1 and 10 carbon atoms; and continuing administration of the methylxanthine compound until a reversal of the arteriosclerosis is detected. In the described methylxanthine compound, $R_2$ is not hydrogen when $R_1$ is hydrogen. Most preferably, $R_1$ is methyl and $R_2$ is a ketone. The ketone group of the particularly preferred embodiment of the invention is 5-hexone.

In still another embodiment of the invention, a method for reversing atheromatous lesions is described. More particularly, a method for reversing atheromatous lesions is claimed comprising identifying a patient having atheromatous lesions; administering to the identified patient a lesion-reversing regimen of a methylxanthine compound having the formula:

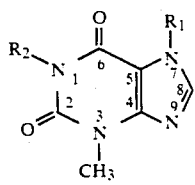

, wherein $R_1$ is hydrogen or methyl and wherein $R_2$ is hydrogen, a ketone or an alkyl having between 1 and 10 carbon atoms; and continuing daily administration of the methylxanthine compound until a reversal of the atheromatous condition is detected. In the described methylxanthine compound, $R_2$ is not hydrogen when $R_1$ is hydrogen. Most preferably, $R_1$ is methyl and $R_2$ is a ketone. The ketone group of this particularly preferred embodiment of the invention is 5-hexone. As defined by the present methods, a lesion-reversing regimen of a methylxanthine compound, such as pentoxifylline, is for humans about 1200 mg of pentoxifylline per day, for between 30-90 days, most preferably for at least 35 days.

Another embodiment of the claimed invention comprises a method for treating or reversing fatty liver tissue damage in a patient comprising: identifying a patient with a compromised liver condition; administering to the identified patient a pharmacologically-acceptable regimen of a methylxanthine compound having the formula:

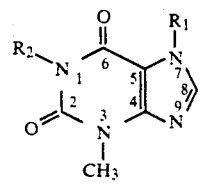

wherein $R_1$ is hydrogen or methyl and wherein $R_2$ is hydrogen, a ketone or an alkyl having between 1 and 10 carbon atoms; and continuing daily administration of the methylxanthine compound until an improvement or a reversal of the fatty liver tissue damage is detected. In the described methylxanthine compound, $R_2$ is not hydrogen when $R_1$ is hydrogen. Most preferably, $R_1$ is methyl and $R_2$ is a ketone. The ketone group of this particularly preferred embodiment of the invention is 5-hexone. As used in the present methods, a "pharmacologically acceptable regimen" is a non-toxic dose of the particularly defined methylxanthine compound. By way of example, where the methylxanthine compound is pentoxifylline, the "pharmacologically acceptable regimen" for an adult human patient would comprise 1200 mg per day for between days. Most preferably, the drug should be administered for at least 35 days.

By way of example, a reversal of the fatty liver tissue damage can be detected by a return to normal of serum transaminase levels or conjugated bilirubin levels in a patient having elevated levels of these compounds. Blood levels of conjugated bilirubin and serum transaminase are markedly elevated in patients having the severe liver pathology described attendant a fatty liver condition.

Conjugated bilirubin is the fraction of serum bilirubin which has been conjugated with glucuronic acid in the liver cell to form bilirubin diglucuronide. Conjugated bilirubin reacts directly with the Erlich diazo reagent.

Increased levels of conjugated bilirubin are found in hepatobilary diseases, especially of the obstructive variety. The condition of bilirubinemia, known as an increase in the concentration of bilirubin in the blood, is associated with pathological conditions where there is interference with the mechanism of excretion in the bile.

The level of conjugated bilirubin in the blood considered normal is very low, approximately between 0.3 and 1.1 mg/dl. The level of transaminase in the blood serum oonsidered normal is approximately between 15 and 40 units aspartate aminotransferase. A return to observable normal blood levels of either conjugated bilirubin or serum transaminase in a patient being treated for fatty liver or other diet-induced liver pathology is considered an indication of an improvement in the fatty tissue damage or as a signal indicating reversal of any liver tissue damage.

Methods of measuring conjugated bilirubin[54, 55, 56] and serum transaminase[57, 58] in a biological sample are well known to those of skill in the art. The use of such described methods to signal an improvement or reversal of the described diseased slates is herein specifically included. These procedures are outlined in the referenced journal articles, which are specifically incorporated herein by reference for such purposes.

In a particularly preferred application of the claimed method, the fatty liver tissue damage which the present compounds are effective in reducing is that liver tissue damage which results from alcohol (i.e., ethanol) ingestion. This condition is commonly known as cirrhosis of the liver. In this particularly preferred embodiment of the invention for the reversal of liver tissue damage, reversal of liver tissue damage may be detected by a decrease in the patients circulating level of particular blood toxins. By way of example, such toxins include elevated blood levels of conjugated bilirubin, (e.g., greater than 1.5 mg/dl) or elevated serum aspartate aminotransferase levels (e.g., =50-300 units or greater than 50 units aspartate aminotransferase).

The described methods of the present invention include the administration of methylxanthine compounds which, in more particularly preferred embodiments, are further defined as comprising an $R_1$ which is a methyl group and an $R_2$ which is a ketone in the displayed $R_1$ and $R_2$ substituted methylxanthine nucleus. Most particularly, when $R_2$ is a ketone, the ketone may be further defined as comprising a keto group separated from the xanthine nucleus by 4 carbon atoms. The keto group, therefore, is described as extending from the fifth carbon atom of a carbon chain extending from the xanthine ring.

The most preferred embodiments of the methods described herein employ the methylxanthine compound pentoxifylline or a compound of which pentoxifylline is a metabolite. Pentoxifylline has the following chemical structure:

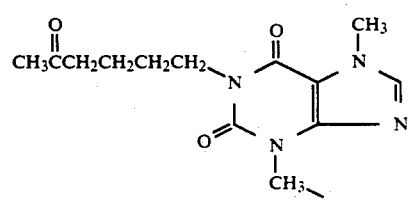

Where pentoxifylline is the particular methylxanthine compound being administered in the various methods described herein, a particular daily regimen of pentoxifylline expected to be effective in promoting the described therapeutic effects, including the improvement or reversal of liver tissue damage, comprises a dose of about 1200 mg/day. This particular dose may be conveniently provided to the patient in three separate doses of about 400 mg each. Such individual doses may preferably take the form of tablets or capsules for oral administration.

Other embodiments of the described therapeutic methods employ a particularly preferred methylxanthine compound defined as comprising pentoxifylline or a bioactive equivalent methylxanthine derivative thereof. More specifically, it is expected that the described derivatives would be effective for the treatment of arteriosclerosis, for reversing atheromatous lesions, and for clearing ethanol or dietary fat-induced liver tissue damage.

It is also expected that compounds of which pentoxifylline is itself a metabolite would be therapeutically valuable in the described methods. By way of example, compounds of which pentoxifylline is itself a metabolite include (1-[5-hydroxyhexyl]-3,7-dimethylxanthine) and (1-[3-carboxypropyl]-3,7-dimethylxanthine).

The surprising and unexpected effects of pentoxifylline on atheromatous lesions (Experimental Example 1) and fatty liver (Experimental Example 2) disclosed herein has not been reported previously. Applicants propose to use ethanol-ingestion techniques to explore the observed exciting phenomenon of pentoxifylline and related compounds in treating ethanol-induced fatty liver tissue damage in animals (Prophetic Experimental Example 3). Applicants' have included prophetic proposals to employ biochemical procedures to examine ethanol-compromised liver metabolic processes, in particular the (NAD/NADH) ratio in rats. These studies are proposed in order to more clearly elucidate the mechanisms underlying the liver-sparing activity of pentoxifylline and its related compounds.

Rabbits employed in the current study were New Zealand male rabbits obtained from Ray Nichols Rabbitry, 1380 West Walton Road, Lumberton, Tex. Rats proposed for use in prophetic Example 3 will be male Sprague-Dawley rats of between 100-150 kg body weight.

Applicants conclude that particular dimethylxanthine derivatives, especially pentoxifylline, are effective in achieving the regression of atherosclerosis (artheromatous lesions) and for the improvement and reverse of fatty liver tissue damage in hypercholesterolemic animals, such as the rabbit. Applicants propose an equally effective therapeutic use of such agents to treat and reverse fatty liver tissue damage and to treat arteriosclerosis (particularly atherosclerosis) in man (Prophetic Experimental Example 4), based upon the presented experimental evidence.

The following examples are presented to describe preferred embodiments and utilities of the present invention and are not meant to limit the present invention unless specifically indicated otherwise in the claims appended hereto.

EXPERIMENTAL EXAMPLE 1

Pentoxifylline in Treating Atheromatic Lesions in Rabbits

The present experiment was designed to determine if treatment of a diet-induced hypercholesteremic animal with pentoxifylline would affect the diet-induced atheromatous lesions formed on the liver tissue of laboratory rabbits. The described methods and the therapeutic agent, pentoxifylline, were utilized in a rabbit model to demonstrate their potential utility in man for the treatment of atherosclerosis, a leading cause of human stroke and heart disease.

All animals were first maintained on a high cholesterol (2%) containing diet for 9 weeks. Untreated control rabbits were then maintained on a normal diet for 9 weeks post-high cholesterol (2%) regimen prior to sacrifice and examination. Treated rabbits were given pentoxifylline daily for a period of 9 weeks along with their normal diet prior to sacrifice and examination.

The results obtained indicate that subsequent treatment of rabbits with pentoxifylline both restored the normal coloration of liver tissues and dissipated the large yellow tissue accumulations of lipids characteristic of those tissues obtained and observed in untreated controls (Table 1).

EXPERIMENTAL PROCEDURE

New Zealand male rabbits, 2.0 to 2.5 kg b.w., were obtained from Ray Nichols Rabbitry, 1380 West Walton Rd., Lumberton, Tex. The rabbits were maintained in individual cages and allowed food and water. After a week of quarantine, the animals were randomly divided into two groups: the first group was placed on a control diet consisting of regular rabbit chow (Group I), whereas a second group was fed an atherogenic diet containing 2% cholesterol (Group II). Total serum cholesterol levels were measured at weekly intervals.

At the end of 9 weeks, half of the animals of each group were sacrificed and the liver and thoracic aortas were examined to assess the effect of high cholesterol (2%) dietary intake.

The rabbits maintained on the atherogenic diet showed atheromatous lesions covering about 80% of the surface area of the aortas. At this time, the remaining half of the cholesterol-fed rabbits were randomly divided into two groups: one group was placed on a normal "control" diet for an additional 9-week period, the second group was placed on a normal "control" diet and given 15 mg/kg/day pentoxifylline orally. Both groups continued on the normal diet for the additional 9-week period. As used in the present invention, the term normal "control" diet is defined as a diet which does not contain the 2% cholesterol levels of the "high-cholesterol" diet.

Total serum cholesterol levels were monitored in all animals at weekly intervals. At the end of the second 9-week period, all rabbits were sacrificed. The thoracic aorta and liver sections of each of the animals were then examined to assess the effect of pentoxifylline on liver and the extent of atheromatous lesions in the hypercholesterolemic rabbits.

Applicants analyzed the data obtained from the quantitative studies of changes in intimal thickness of the atherosclerotic lesions in control and experimental (2% cholesterol-ingesting) animals. Histological procedures have been developed by Applicants which provide the means by which intimal thickness within specified areas of aortic vessel wall were quantified. This technique was utilized extensively in the comparison of changes in intimal thickness of atheromatous lesions and plaques.

HISTOLOGY OF ATHEROMATOUS LESIONS

A segment of about 5 ml in surface area was excised from each of the atherosclerotic lesions. The tissues were cut perpendicular to the surface and stained with Hematoxylin and Eosin. The stained histological sections were photographed at a magnification of X200. From these pictures the thickness of the intima from the surface down to the external elastic membrane was measured. The reduction in intimal thickness of pentoxifylline treated cholesterol-fed rabbits was compared to that of control and untreated cholesterol-fed rabbits.

Total cholesterol content of aortic tissues from cholesterol-fed and pentoxifylline treated cholesterol-fed rabbits was measured on chloroform:methanol (2:1, vol./vol.) extracts of intima media using a colorimetric method.

RESULTS

Figure 2:
FIG. 2. This section is taken from thoracic aorta of an untreated cholesterol-fed rabbit (fed 2% cholesterol enriched diet for 9 weeks). There is a marked increase in giant smooth muscle cell proliferation and very little elastic tissue in the media. This section also shows fibroelastic intimal thickening. (Gomori's trichrome stain, 50X).
Figure 3:
FIG. 3. This section is taken from the thoracic aorta of a pentoxifylline-treated cholesterol-fed rabbit (fed 2% cholesterol enriched diet for 9 weeks thereafter given 15 mg/kg/day of pentoxifylline orally in addition to standard rabbit chow for additional 9 weeks). This section shows substantial reduction in the aortic intimal thickness with some foam cells and lipid deposits demonstrated in the subendothelial zone. (Hematoxylin Eosin stain, 50X).
Figure 4:
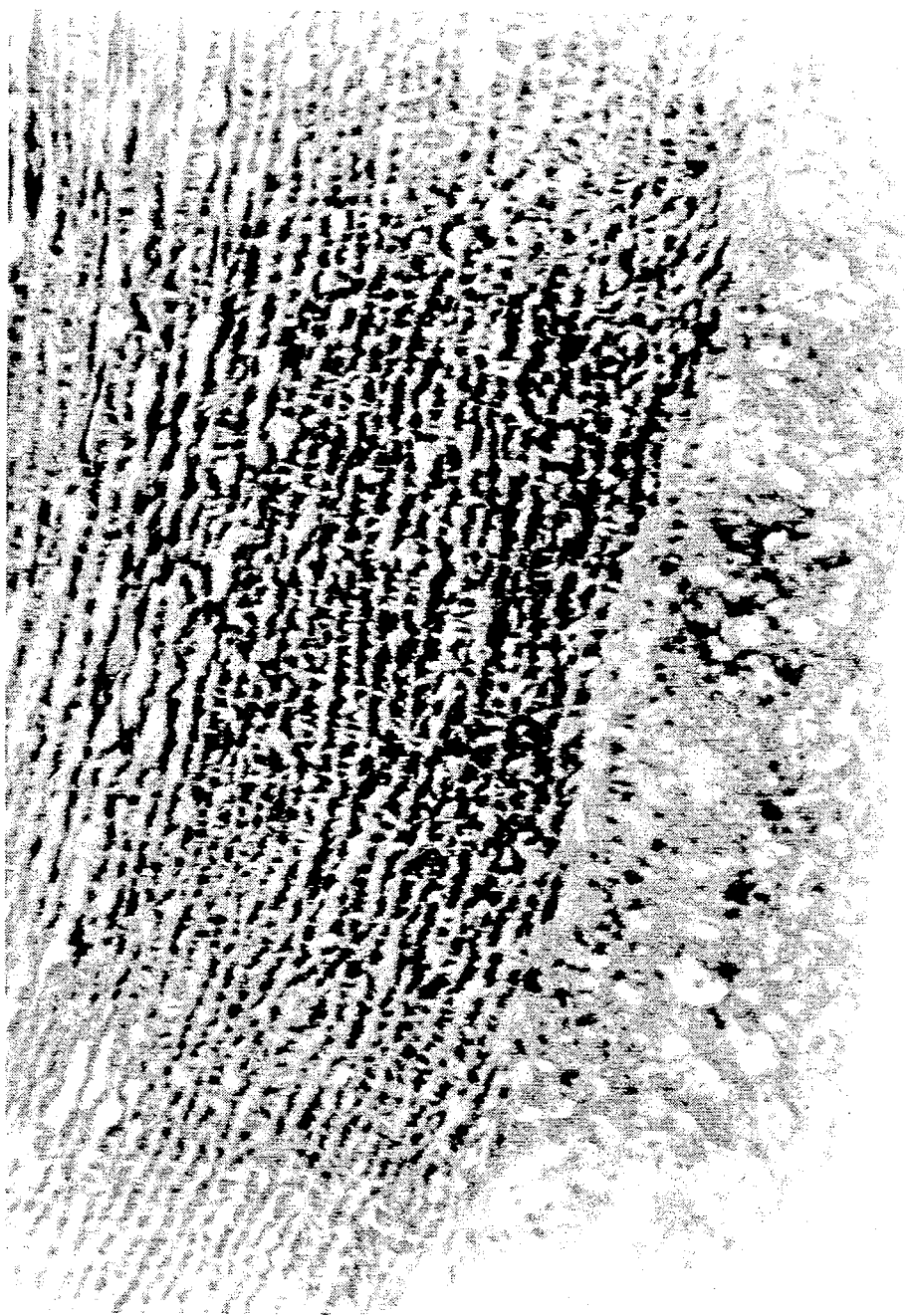
FIG. 4. This section is taken from the thoracic aorta of a pentoxifylline treated cholesterol-fed rabbit (fed 2% cholesterol enriched diet for 9 weeks; thereafter given 15 mg/kg/day of pentoxifylline orally, in addition to standard rabbit chow for additional 9 weeks). This section shows reduction in the fibro-elastic intimal thickness with some foam cells and lipid deposits in the subendothelial zone. (Gomori's trichrome stain, 50X).

Cholesterol-fed rabbits maintained on a subsequent normal diet showed little change in the extent of atherosclerosis after the second 9-week period. In these animals, atheromatous lesions were characterized by marked proliferation of endothelial and smooth muscle cells of aorta, the appearance of large quantities of giant smooth muscle cells and foam cells and thickening of the intima (FIG. 1 and 2). In contrast, the pentoxifylline-treated rabbits showed substantial reduction in intima thickness and in the quantity of smooth muscle and foam cells of the intima (FIG. 3 and 4). These animals also showed substantial reduction of collagen and rearrangement of proliferated smooth muscle cells of the intima where endothelial cells had either been damaged or had disappeared.

The data observed from these quantitative studies have shown a pronounced difference in the reduction of arterial intimal thickness (Table 1). As demonstrated in Table 1, intimal thickness was reduced as a result of daily pentoxifylline treatment. Average PTX reduction of intimal thickness in all animals treated with pentoxifylline (Group II, N=6) was 32.4% compared to non-pentoxifylline treated control animals (Group I, N=6).

TABLE I

Arterial Intimal Thickness in Cholesterol-fed and Trental ® (PTX) Treated Cholesterol-fed Rabbits

| Group | Number of Rabbits | Weeks on Cholesterol Diet | Weeks on Normal Diet | Weeks Treated with PTX | Intimal Thickness (um) Mean* |
|---|---|---|---|---|---|
| I | 1 (Exp. 1) | 9 | 9 | 0 | 450 |
|  |  |  |  |  | 315 |
|  |  |  |  |  | 470 |
|  |  |  |  |  | 450 |
|  |  |  |  |  | 421* |
|  | 2 (Exp. 2) | 9 | 3** | 0 | 380 |
|  |  |  |  |  | 430 |
|  |  |  |  |  | 410 |
|  |  |  |  |  | 406 |
|  |  |  |  |  | 407* |
|  | 3 (Exp. 2) | 9*** | 0 | 0 | 341 |
|  |  |  |  |  | 315 |
|  |  |  |  |  | 330 |
|  |  |  |  |  | 406 |
|  |  |  |  |  | 348* |
| II | 1 (Exp. 1) | 9 | 9 | 9 | 224 |

TABLE 1-continued

Arterial Intimal Thickness in Cholesterol-fed and Trental ® (PTX) Treated Cholesterol-fed Rabbits

| Group | Number of Rabbits | Weeks on Cholesterol Diet | Weeks on Normal Diet | Weeks Treated with PTX | Intimal Thickness (um) Mean* |
|---|---|---|---|---|---|
|  |  |  |  |  | 420 |
|  |  |  |  |  | 242 |
|  |  |  |  |  | 202 |
|  |  |  |  |  | 272* |
|  | 2 (Exp. 1) | 9 | 9 | 9 | 117 |
|  |  |  |  |  | 240 |
|  |  |  |  |  | 315 |
|  |  |  |  |  | 200 |
|  |  |  |  |  | 218* |
|  | 3 (Exp. 2) | 9 | 9 | 9 | 245 |
|  |  |  |  |  | 305 |
|  |  |  |  |  | 320 |
|  |  |  |  |  | 312 |
|  |  |  |  |  | 295* |

Each value represents the average of 3-4 measurements from aortic sections of each rabbit.
**death after 3 weeks on normal diet.
***death after 9 weeks on 2% cholesterol enriched diet.
Pentoxifylline-treated rats (Group II) demonstrated a 32.4% reduction in intimal thickness compared with non-pentoxifylline treated control animals (Group I).

EXPERIMENTAL EXAMPLE 2

Effect of Pentoxifylline on Fatty Liver

The present experiment was designed to determine if pentoxifylline treatment had any effect on reversing dietary induced fatty liver conditions. Pentoxifylline was utilized in a rabbit model to demonstrate the potential utility of using the described methods for treating fatty liver in humans.

EXPERIMENTAL PROCEDURE

One group of rabbits were maintained on a high (2%) cholesterol diet for 9 weeks as described in Experimental Example 1. Another group of rabbits was maintained on a normal diet (regular rabbit chow). Total serum cholesterol levels were measured at weekly intervals. At the end of the first 9 week period, half of the rabbits from each group were sacrificed. The liver specimens from each animal were examined to assess the effect of cholesterol. The rabbits maintained on the atherogenic diet showed well developed fatty livers and atheromatous lesions covering about 80% of the surface area of the aortas.

The remaining half of the cholesterol-fed rabbits were then randomly divided into two groups: one group was placed on a normal diet (as described in Experimental Example 1) for an additional 9-week period, the second group was placed on a normal diet and given 15 mg/kg/day pentoxifylline orally. Both groups continued on the normal diet for the additional 9-week period. Total serum cholesterol levels were monitored in all animals at weekly intervals.

At the end of the second 9-week period, all rabbits were sacrificed and liver sections examined to assess the effect of pentoxifylline on liver lipid content in hypercholesterolemic rabbits.

RESULTS

The total cholesterol values of liver tissue extracts obtained from this study demonstrate that lipid deposition in liver tissue was more prevalent in non-pentoxifylline treated cholesterol-fed rabbits than in pentoxifylline-treated, cholesterol-fed rabbits. As demonstrated in Table II. PTX treatment resulted in a reduction of total liver lipid in all animals. The average reduction in liver lipid after pentoxifylline treatment was 39% (N=6) compared to non-pentoxifylline treated rabbits (N=6).

The reduction in the total liver lipid values of liver tissue extracts from PTX-treated animals clearly demonstrated that lipid deposition in liver tissue was more prevalent in non-treated cholesterol-fed rabbits than in pentoxifylline treated cholesterol-fed rabbits (Table II).

TABLE II

Total Lipid in Rabbit Liver Tissue

| Group | Number of Rabbits | Weeks on Cholesterol Diet | Weeks on Normal Diet | Weeks Treated with PTX | Lipid Content (mg/g tissue) Mean* |
|---|---|---|---|---|---|
| I | 1 (Exp. 1) | 9 | 9 | 0 | 197.60 |
|   |            |   |   |   | 221.65 |
|   |            |   |   |   | 209.62* |
|   | 2 (Exp. 2) | 9 | 3** | 0 | 226.80 |
|   |            |   |   |   | 187.50 |
|   |            |   |   |   | 207.15* |
|   | 3 (EXp. 2) | 9*** | 0 | 0 | 265.75 |
|   |            |   |   |   | 207.75 |
|   |            |   |   |   | 236.75* |
| II | 1 (Exp. 1) | 9 | 9 | 9 | 137.50 |
|    |           |   |   |   | 134.00 |
|    |           |   |   |   | 135.75* |
|    | 2 (Exp. 1) | 9 | 9 | 9 | 100.00 |
|    |           |   |   |   | 142.77 |
|    |           |   |   |   | 121.38* |
|    | 3 (Exp. 2) | 9 | 9 | 9 | 121.70 |
|    |           |   |   |   | 165.10 |
|    |           |   |   |   | 143.40* |

Each value represents mean of 2 liver extract measurements from each rabbit.
**death after 3 weeks on normal diet.
***death after 9 weeks on 2% cholesterol enriched diet.
Average Reduction in liver lipid = 39%.
Pentoxifylline-treated animals (Group II, N = 6) demonstrated a 39% reduction in liver lipid compared with the non-pentoxifylline treated animals (Control Group I, N = 6).

Histology

Figure 5:
FIG. 5. This section is taken from the liver of an untreated cholesterol-fed rabbit (fed 2% cholesterol enriched diet for 9 weeks thereafter cholesterol diet substituted with standard rabbit chow for additional 9 weeks). It shows closely packed and enlarged hepatic cells. Most sinusoid structures have disappeared but the remaining ones are severely damaged. The hepatic cells show a large amount of lipid deposits with degeneration as a result of malnutrition. Overall liver architecture is poorly delineated. (Hematoxylin and Eosin stain, 50X).
Figure 6:
FIG. 6. This section is taken from the liver of an untreated cholesterol-fed rabbit (fed 2% cholesterol enriched diet for 9 weeks). The hepatic cells show well defined degeneration as a result of malnourishment. Intracellular and extracellular lipid deposits are prominent. (Gomori's trichrome stain, 50X).

The liver sections from untreated hypercholesterolemic rabbits revealed substantial injury and changes in the overall liver morphology (FIG. 5 and 6). These sections showed closely packed, enlarged hepatic cells and loss of canaliculi vessel spaces between adjacent swollen giant liver cells. Most of these liver sections showed compressed portal tracks and severely damaged biliary structures indicating a compromised microcirculation.

The strong indication of the pentoxifylline effect was first observed in gross liver specimens obtained from cholesterol-fed rabbits treated with pentoxifylline. The appearance of color, texture and size of the liver from PTX treated animals approached normal when compared with the liver of untreated hypercholesterolemic rabbits. Untreated hypercholesterolemic rabbits showed a pale, hardened and enlarged aspect.

Figure 7:
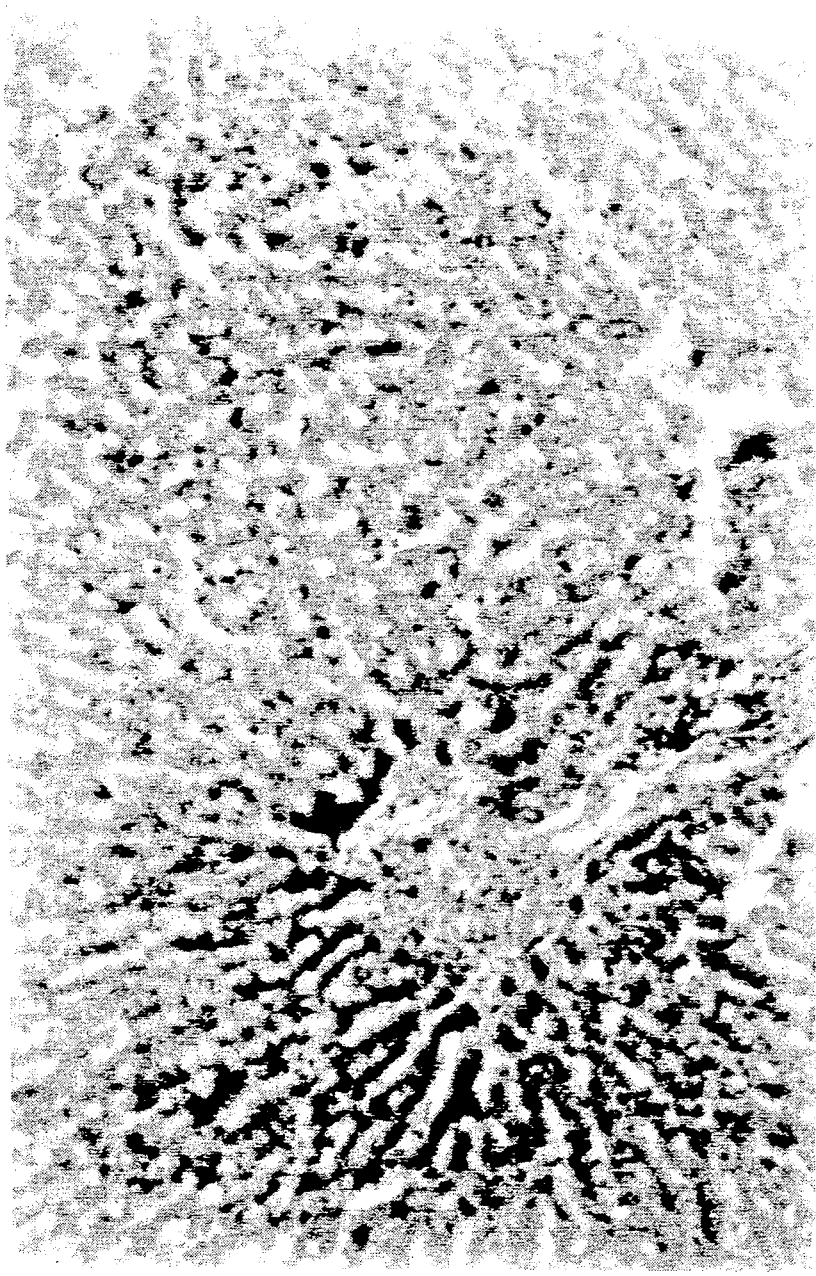
FIG. 7. This section is taken from the liver of a pentoxifylline-treated cholesterol-fed rabbit (fed 2% cholesterol enriched diet for 9 weeks thereafter given 15 mg/kg/day of pentoxifylline orally in addition to standard rabbit chow for additional 9 weeks). This section shows numerous sinusoidal spaces and hepatic cells which look normal. The liver cells contain little or no lipid deposits and canaliculi appear in the areas close to the central vein. The portal canal contains the intralobular bile duct together with branches of portal vein and hepatic artery, which appear normal. (Hematoxylin and Eosin stain, 50X).
Figure 8:
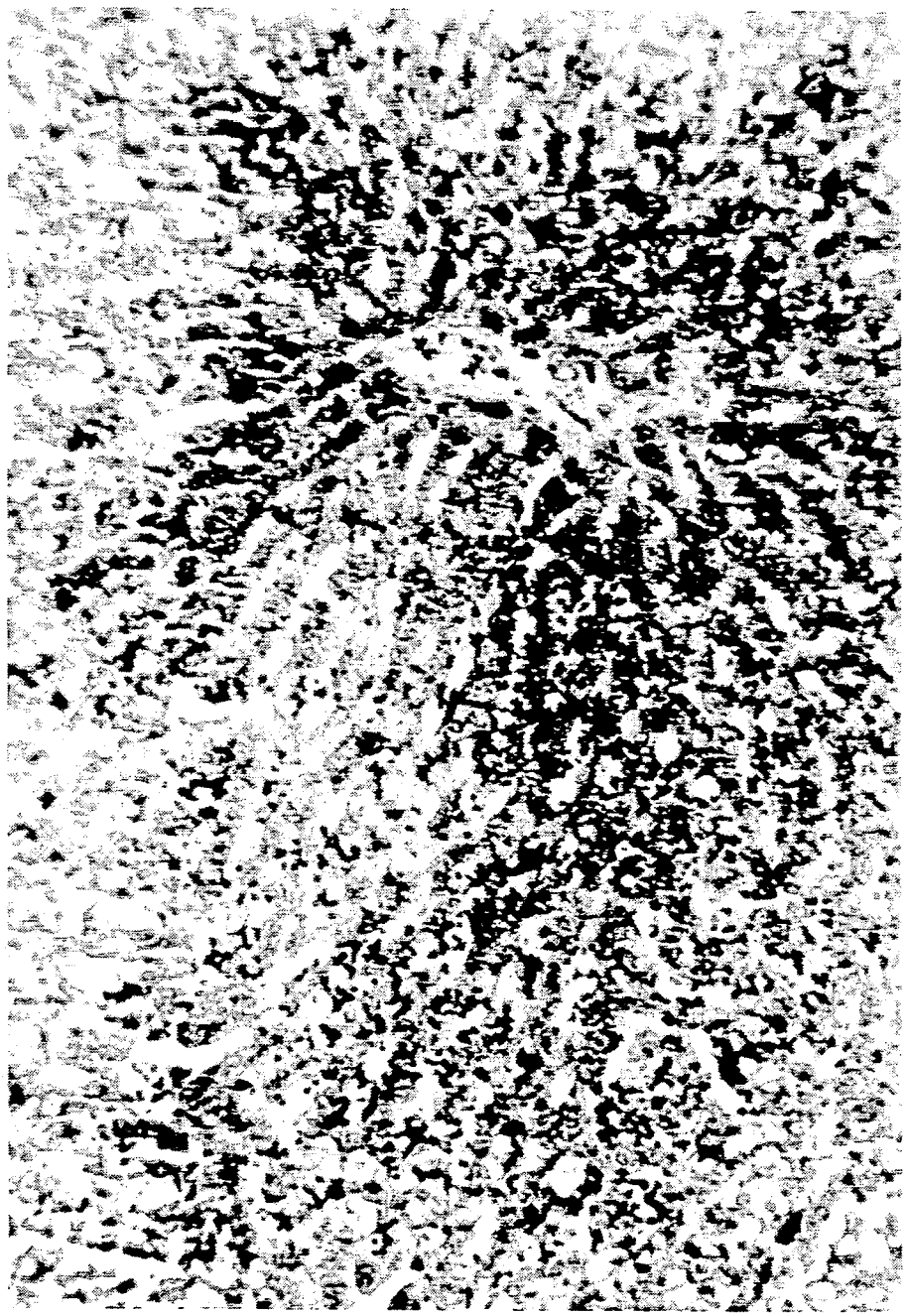
FIG. 8. This section is taken from the liver of a pentoxifylline treated cholesterol-fed rabbit (fed 2% cholesterol enriched diet for 9 weeks thereafter given 15 mg/kg/day of pentoxifylline orally in addition to standard rabbit chow for additional 9 weeks). Liver cells show very little lipid deposits. Overall liver architecture is very well delineated, showing well structured canaliculi in the areas close to the central vein. (Hematoxylin and Eosin stain, 60X).

Paraffin embedded sections of pentoxifylline-treated rabbit liver sections revealed substantial improvement of the liver architecture and overall morphology. These liver sections showed numerous sinusoidal spaces and hepatic cells around blood vessels (FIG. 7 and 8).

Figure 9:
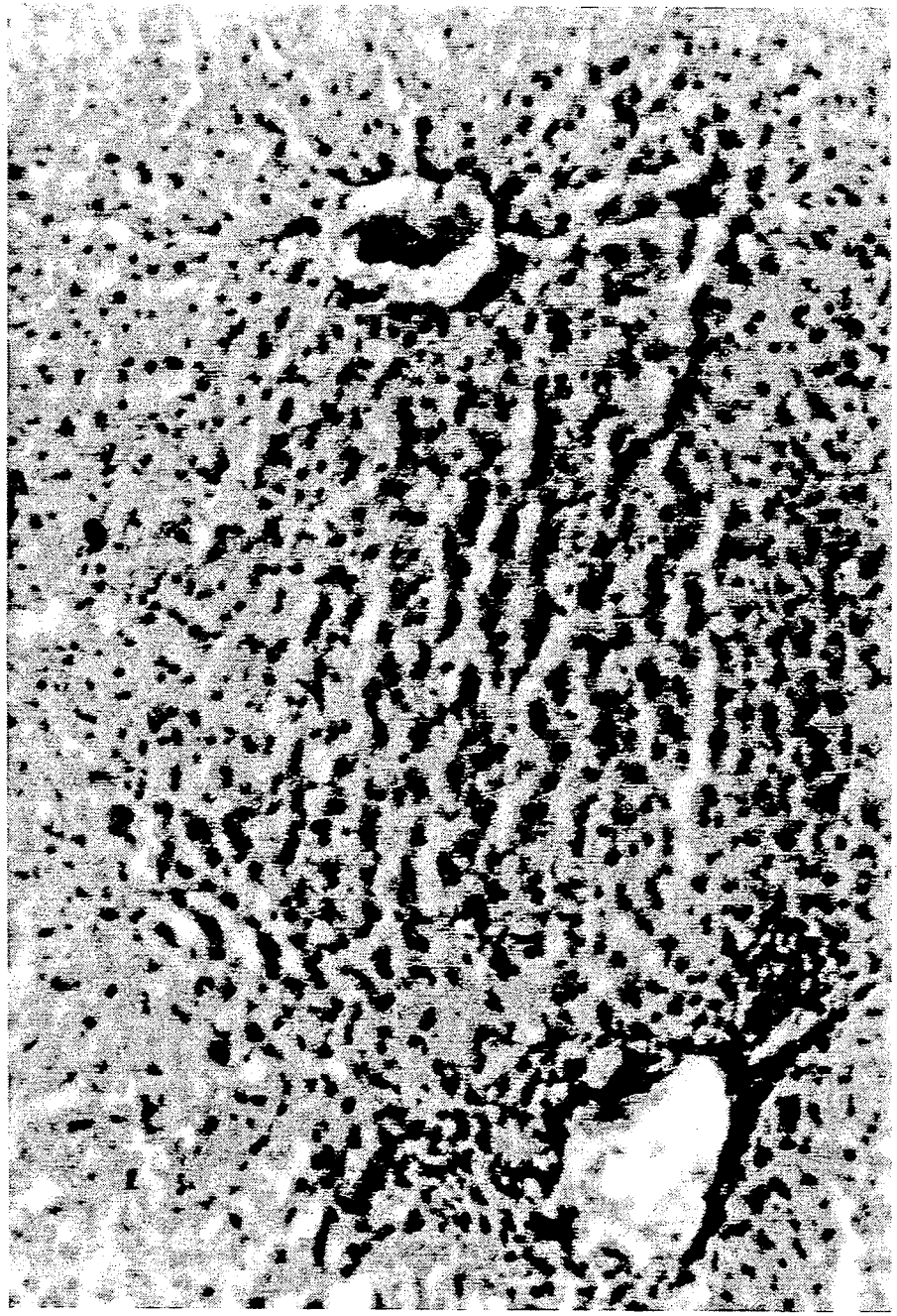
FIG. 9. This section is taken from the liver of a pentoxifylline-treated cholesterol-fed rabbit (fed 2% cholesterol enriched diet for 9 weeks thereafter given 15 mg/kg/day of pentoxifylline orally in addition to standard rabbit chow for additional 9 weeks). This section shows a large number of hepatic cells around the blood vessels and portal areas, which are free of fatty deposits. It also shows marked reduction of lipid deposits in hepatocytes in almost all hepatic lobules. (Oil Red O stain, 50 X).
Figure 10:
FIG. 10. This section is taken from the liver of a pentoxifylline-treated cholesterol-fed rabbit (fed 2% cholesterol enriched diet for 9 weeks). This section shows marked reduction in lipid deposits in hepatocytes and in ares around the blood vessels and portal region. (Oil Red O stain, 60X).
Figure 11:
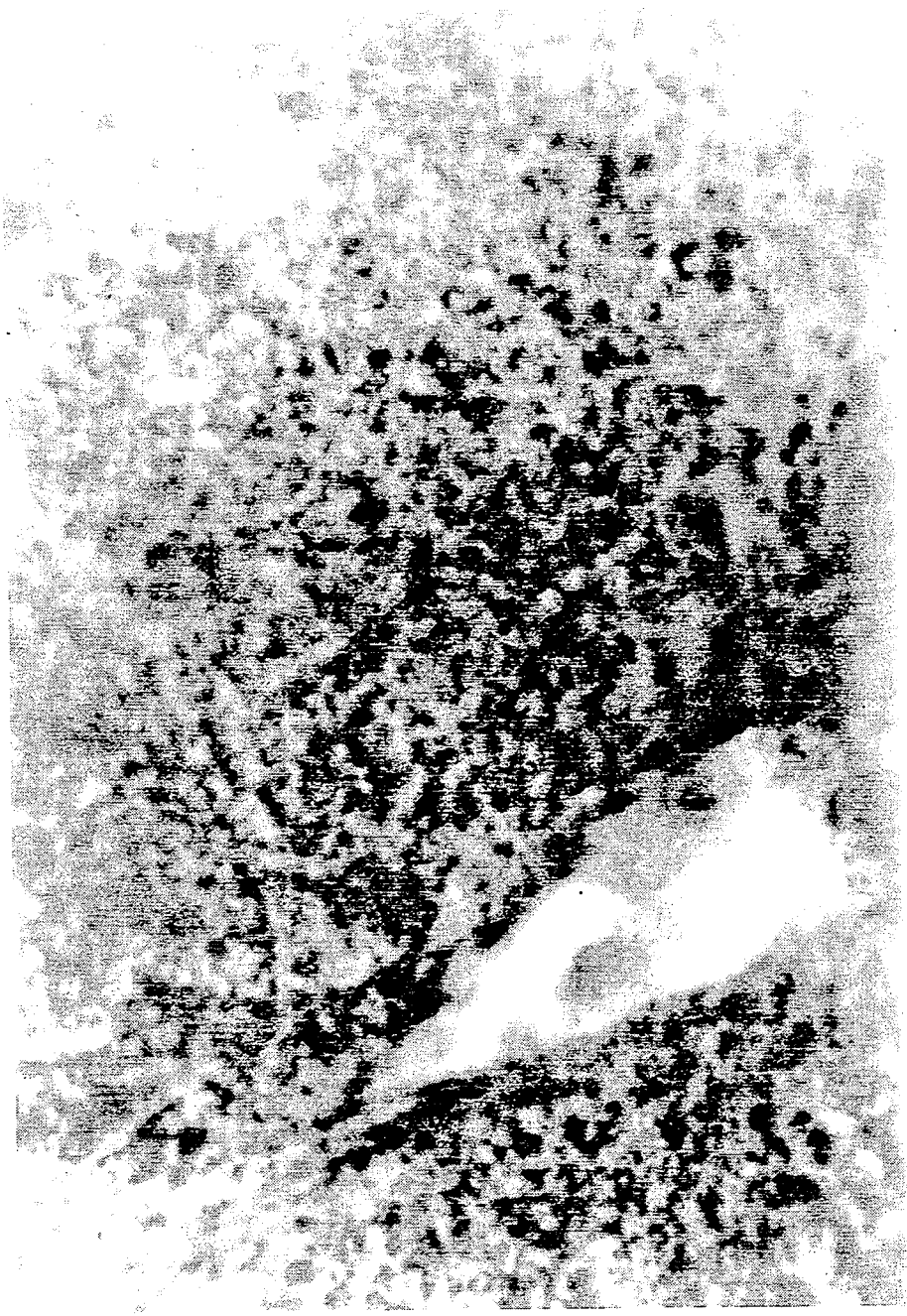
FIG. 11. This section is taken from the liver of an untreated cholesterol-fed rabbit (fed 2% cholesterol enriched diet for 9 weeks thereafter cholesterol diet substituted with standard rabbit chow for additional 9 weeks). The whole specimen absorbed Oil Red O stain, which indicates the presence of intracellular and extracellular lipid accumulation. (Oil Red O stain, 50X).

Frozen liver sections stained with Oil Red O taken from hypercholesterolemic rabbits treated with pentoxifylline showed a large number of hepatic cells around the blood vessels and portal areas which appeared to be free of fatty deposits (FIG. 9 and 10). Liver sections from hypercholesterolemic rabbits showed a large number of hepatic cells uniformly containing fatty deposits throughout the whole specimen (FIG. 11).

The results of these investigations showed a marked alteration in the entire hepatic structure accompanied by degenerative and proliferative changes that reversed to a morphologically and pathophysiologically normal appearing liver after treating with PTX for three months These data demonstrate that pentoxifylline is effective in causing regression of atherosclerosis and clearance of fatty liver in diet-induced hypercholesterolemic rabbits.

PROPHETIC EXPERIMENTAL EXAMPLE 3
PENTOXIFYLLINE FOR THE REVERSAL OF ALCOHOL-INDUCED FATTY LIVER IN RATS

The present experiment was designed to determine if pentoxifylline would be effective to reverse an alcohol diet-induced fatty liver condition in rats. Pentoxifylline was utilized in treating alcohol-induced fatty liver in a rat model to demonstrate its potential utility as a treatment in alcohol-induced fatty liver tissue damage in humans. Specifically, Applicants will investigate the effect of pentoxifylline on fatty liver produced by chronic administration of ethanol. Applicants will also investigate the direct and/or indirect effects of pentoxifylline on the concentrations and relative proportions of pyridine nucleotides (NAD+, NADH$_2$, NADP+ and NADPH$_2$) in livers of ethanol-treated male rats.

Other objectives of this study are to investigate the correlation between the particular pentoxifylline dose required to effect a reversal of the fatty liver condition. The interaction between accumulated fat and other structural and functional alterations, and the consequent enzyme activities, will also be examined.

Applicants, in this proposed study, also seek to measure the free cytosolic [NAD]/NADH ratio and mitochondrial pyruvate level and the effect of pentoxifylline on the overall [NADP]/NADH ratio in liver of experimental and control animals.

In addition, Applicants also have outlined experiments to accomplish the following:

(1) to measure the free cytosolic [NAD]/NADH ratio and mitochondrial pyruvate level and the effect of pentoxifylline on the overall [NADP]/[NADH]ratio in liver of experimental and control animals.

(2) to determine the change of the rate of oxidation of fatty acids under the influence of pentoxifylline by quantitating ATD, ADP, AMP, Pi and NH production.

(3) to analyze histopathological changes and determine the fat content in experimental and control rats.

Methods of Procedure

Male Sprague-Dawley rats of between 100–150g body weight will be used for all experiments. Prior to the feeding of a liquid diet containing ethanol, animals will be maintained on Purina laboratory chow and tap water ad libitum for 2 weeks to prevent respiratory infection. The animals will be divided randomly into five groups of ten each. Rats will be housed two to a cage and fed a liquid diet in drinking tubes as the only source of food and water.

GROUP A—10 rats will be fed a liquid control diet and maintained throughout the experiment.

GROUP B1—10 rats will be fed a liquid diet with carbohydrate isocalorically replaced by ethanol to the extent of 36% of total calories.

GROUP B2—15 rats will be fed same diet as B1. This group will be used for determining the effect of pentoxifylline after fatty liver has been developed.

GROUP C—10 rats treated with ethanol diet as in B1, with the addition of 24 mg/kg pentoxifylline.

GROUP D—10 rats fed control diet with the addition of 24 mq/kq pentoxifylline.

Liquid diets will be prepared in aocordance with the procedure described by DeCarli and Lieber[2].

DeCarli and Lieber[2] found that fatty livers developed after only 24 days on the ethanol liquid diet. Applicants propose to sample one rat from each ethanol-fed group after 24 days to determine if fatty livers do indeed develop (following previous dissection and testing procedure described in our previous protocol for rabbits). Rats will be sacrificed by decapitation followed by rapid extirpation of the liver and withdrawal of appropriate blood samples. If significant fatty livers are found, then additional animals will be withdrawn from each of the other groups and sampled as described. In this case, Group B-2 will be divided in three, five rats will be continued on the ethanol diet, five rats will be given the ethanol diet plus 24 mg/kg pentoxifylline and five rats will be taken off the ethanol diet and placed on the standard diet and given 24 mg/kg pentoxifylline per day.

The remaining rats will be continued on the same protocol for an additional 24 days, at which time another rat from each ethanol group will be examined as described above. At this time, it is expected that a frank, pre-cirrhotic liver will have developed. However, if not, the remaining animals will be continued on protocol for another 24 days, at the end of which time all animals will be either sacrificed for testing (Groups B-1 and C), continued for additional study (Group B-2) or held for additional studies (Groups A and D).

Procedure of Measurements of Intracellular NADH

At the end of the experimental period, control and experimental rats will be decapitated, the abdomen opened, and a portion of the liver will immediately be compressed (with aluminum clamps precooled in liquid nitrogen) and removed for further processing. The frozen samples will be weighed and transferred to a precooled mortar together with a quantity of liquid nitrogen, and ground to a dry frozen powder. One half of the powder will be used for the preparation of perchloric acid protein-free extract, and the other half, for the extraction of water-soluble proteins. The frozen tissue powder will be weighed in 9 vol. of the homogenization medium at 0°-2° C. and homogenized immediately in a chilled glass-teflon homogenizator and centrifuged at 12,000 g for 30 minutes at 0°-2° C. The supernatant will be used as a source of cytosolic enzymes, and for the determination of ATP, ADP, AMP, Pi and $NH_3$.

1. Preparation of Protein Free Extracts

For the preparation of protein-free extracts and assay of metabolites, the same procedure will be used as described for preparation of protein extracts except isocitrate will be determined as glucose-6-phosphate with isocitrate dehydrogenase instead of glucose-6-phosphate dehydrogenase. The protein concentrations in the enzyme extracts will be measured colorimetrically with serum albumin as standard using the procedure of Lowry, et al.[44]

2. Enzyme Assays

All enzyme activities will be determined in the supernatant fraction of liver incubated at 20° C. in an assay mixture containing 0.1 M KCl, 20 mM Tris-HCL (pH 7.5), 5 mM $MgSO_4$., 0.5 mM NADP and 100 µl extract. To measure the activities of glucose-6-phosphate dehydrogenase, malic enzyme and NADP isocitrate dehydrogenase, either 10 mM glucose-6-phosphate, 5 mM L-malate or 2.5 mM D,L-isocitrate respectively, added to the assay mixture. The reaction will be followed by NADP reaction at 340 nm. Glutamate, pyruvate and isocitrate will be determined fluorimetrically[39]. Other metabolites will be measured by spectrophotometric assay techniques[40, 45].

3. Calculations of Concentrations and Relative Proportions of Pyridine Nucleotides The cytoplasmic free [NAD]/[NADH] will be calculated from the lactate dehydrogenase reaction. The cytoplasmic free [NADP]/[NADPH] ratio will be calculated from the isocitrate dehydrogenase reaction, this ratio will then be calculated from the malic enzyme reaction. The mitochondrial free [NAD]/[NADH] ratio will be calculated from the 3-hydroxybutrate dehydrogenase glutamate dehydrogenase reactions.

Measurement of Ethanol Concentration

50 µl blood samples will be obtained in heparinized micropipets from free-flowing blood obtained by repeatedly clipping the tip of the tail. The blood sample will be diluted with 250 µl deionized water (0° C.). The samples will be capped and placed on ice for 15 minutes. 5 ml 0.2 Tris-acetate buffer pH 9.5 will be added. The mixture will be centrifuged (3,000 g) at 0° C. for 15 minutes. The Tris will be recrystallized from acetone to remove traces of ethanol. Ethanol will be determined spectrophotometrically on the clear supernate with yeast alcohol dehydrogenase[45]. The ethanol concentration will be determined for each animal by linear regression analysis.

Determination of Lipid Content of Liver Tissues

The total lipid content of liver tissues of sacrificed control and experimental rats will be determined by the method developed in our laboratory. Liver tissues will be extracted using chloroform:methanol (2:1, vol/vol). The lipid content will be determined colorimetrically[46].

Hisotpathological Analysis

Liver tissue specimens from sacrificed control and experimental animals will be removed for histopathological studies. Tissue samples will be fixed by immersion in 3% glutaraldehyde for general morphological analysis. For light microscopic examinations, three samples from each liver tissue specimen will be fixed in 10% neutral formalin. The sections will then be stained with Hematoxylin and Eosin to differentiate the various components of the liver sections.

PROPHETIC EXPERIMENTAL EXAMPLE 4
PROPOSED USE IN HUMANS FOR THE TREATMENT OR ARTERIOSCLEROSIS AND FATTY LIVER IN HUMANS

From the results obtained in rabbit in vivo studies with pentoxifylline, Applicants propose the future use of pentoxifylline and its bioactive equivalent methylxanthine derivatives in the treatment and to effect the regression of atherosclerosis and the clearance of fatty liver in humans. As noted supra, chornic intake of ethanol is known to cause fatty liver both in experimental animals and humans.

Specifically, the postulated method of treating dietary-induced pathogenic liver tissue conditions in humans comprises identifying a patient suffering from a fatty liver condition, administering a therapeutic agent comprising pentoxifylline, or a bioactive equivalent methylxanthine derivative thereof, to the identified patient, and continuing daily administration of the therapeutic agent until a therapeutic improvement of the fatty liver condition is detected. Most particularly, the administration of the therapeutic agent is continued utnil a reversal of the pathogenic liver condition is detected.

Even more specifically, the inventive method as applied to humans involves identifying a patient having a diet-induced fatty liver condition and administering to the identified patient a pharmaceutically acceptable amount of pentoxifylline, or a bioative equivalent methylxanthine derivative thereof. Other compounds of which pentoxifylline is itself a metabolite would also be expected to comprise a therapeutically valuable treatment for atherosclerotic conditions and fatty liver tissue damage in humans.

Applicants additionally propose a method for reversing dietary-induced fatty liver conditions in humans comprising identifying a patient with a fatty-liver condition and administering to that patient a fatty-liver reducing amount of pentoxifylline or a bioactive equivalent methylxanthine derivative thereof. A bioactive equivalent methylxanthine derivative of pentoxifylline is more particularly defined as a compound which is capable of effecting a reversal of tissue damage caused by lipid deposition or chronic alcohol ingestion.

The present invention also comprises a prophylactic treatment to prevent dietary induced fatty-liver conditions in humans comprising administering to a patient a prophylactically-effective amount of pentoxifylline or a bioactive methylxanthine derivative thereof, or a compound of which pentoxifylline is itself a metabolite.

The above-described methods of treating, reversing and preventing dietary-induced fatty-liver conditions in humans similarly may be employed in methods to treat, reverse and prevent atheromatous lesions and arteriosclerosis.

For the proposed methods described herein for treating, reversing and preventing dietary-induced fatty liver conditions, atheromatous lesions or arteriosclerosis in humans, the treatment regimen which is postulated to be effective in precipitating the described therapeutic results is comprised of administering between 300-600 mg pentoxifylline, or a bioactive-equivalent methylxanthine derivative thereof, to the patient three times a day. Most preferably, the therapeutic agent is administered orally in the form of a tablet or capsule.

Those methylxanthine compounds exhibiting bioactive lipid-clearing and tissue normalizing properties contemplated a suitable therapeutic agent for the described methods would include any natural metabolite of pentoxifylline or any substance of which pentoxifylline itself is a metabolite.

Pentoxifylline is a compound currently approved by the FDA for human use. Pentoxifylline has, until this time, been used in the treatment of patients with intermittent claudication due to chronic occlusive arterial disease. Pentoxifylline is also known to reduce blood viscosity by virtue of its effect on erythrocyte flexibility. However, never before have the particular methylxanthine, pentoxifylline, or pentoxifylline-like methylxanthine been proposed as effective in the treatment of fatty liver and reversal/treatment of atheromatous lesions. From the experimental evidence already obtained in rabbits, Applicants postulate the use of such an agent would be effective in the treatment of lipid-induced tissue damage in humans.

From our animal studies, we conclude that pentoxifylline and bioactive-equivalent methylxanthine derivatives thereof would be capable of effecting regression of atherosclerosis and fatty liver tissue damage in humans. Many lipid deposit areas of aortic atheromatous lesions in human have surface defects in the form of pits and vesicular blebs.[20] Applicants postulate that these morphological findings indicate that direct accumulation of extracellular lipid from interstitial lipoproteins are a major process in the atheromatous lesion formation in humans. Similar diseased tissue morphology has been observed by Applicants in rabbits, and therefore Applicants hypothesize pentoxifylline would be equally as effective in reducing fatty atherosclerotic lesionary in human tissue.

While not intending to be held to any particular theory, a dynamic state of ongoing physical/metabolic transformation of extracellular lipid deposits play a role in the early stages of the lesion. Applicants conclude that:

(1) the formation of lipid-rich core is clearly evident in the development of many raised lesions and plaques;
(2) the consistent association between the superficial layer of foam cells and the deep-lying lipid-rich core raises the possibility of an influence, possibly indirect, of foam-cell lipid metabolism on core formation; and
(3) the fiber-lipid lesion may represent one stage in a potential transitional morphological sequence between fatty streak and fibrous plaque.

BIBLIOGRAPHY

The following references are specifically herein incorporated by reference in pertinent part, as appropriate, in the present Specification.
1. Lieber et al., (1965), *J. Clin. Invest.*, 44:1009–21.
2. DeCarli et al., (1967), *J. Nutr.*, 91:331–6.
3. Pporta et al., (1965), *Lab. Invest.*, 14:1437–55.
4. Klatskin, G., (1961), *Gastroenterology*, 41:443–57.
5. LeBach, W. K., (1975), *Ann. NY Acad. Sci.*, 252:85–94.
6. Smith et al., (1982), *Lipids*, 180:124–8.
7. Mendelson et al., (1973), *Science*, 180:1371-r.
8. Lieber et al., (1970), *Am. J. Clin. Nutr.*, 23:474—8.
9. Scheig, R., (1971), *Gastroenterology*, 60:751.
10. Brunengraber et al., (1974), *Alcohol and Aldehyde Metabolizing Systems*, New York, NY: Academic Press, pp. 329–37.
11. Blomstrand et al., (1973), *Life Sci.*, 13:1131–41.
12. Kosenko et al., (1985), *Int. J. Biochem.*, 17:895–902.
13. Kalan et al., (1970), *Can. J. Physiol. Pharmacol.* 48:542–9.
14. Forsander, O. A., (1970), *J. Stud. Alcohol*, 31:550–70.
15. Christensen et al., (1986), *In: Biochemistry and Pharmacology of Ethanol.*, New York, NY: Plenum Press, 1:191–247.

16. Cherrick et al., (1965), *Biochem. Biophys. Acta.*, 107:29-37.
17. Lieber et al., (1961), *Clin. Invest.*, 40:394-9.
18. Lieber, C. S., (1968), *Adv. Intern. Med.*, 14:151-99.
19. Brown and Goldstein, (1983), *Ann. Rev. Biochem.*, 52:223-61.
20. Goodman & Gillman, (1985), *In: The Pharmacolooical Basis of Therapeutics*, 7th ed., Chapt. 25, 34.
21. Altschul et al., (1955), *Arch. Biochem. Biophys.* 55(54):558-9.
22. Grundy et al., (1981), *J. Lipid Res.*, 22:24-36.
23. Gey et al. (1971), *In: Metabolic Effects of nicotinic Acid and its Derivatives*, Hans Huber Publishers, Bern.
24. Olver et al., (1978), *Br. Heart Jr.*, 40:1069-1118.
25. Symposium (Various authors) *Gemfibrozil: a new lipid lowering agent, Proc. R. Soc. Med.*, (1976), 69 Suppl. 2:1-20.
26. Moor, S. (1979), *Exp. Mo.. Pathol.*, 31:182-90.
27. Lacson et al., (1966), *J. Artherscelr. Res.*, 6:277-82.
28. Kjelden et al., (1969), *J. Artherosclr. Res.*, 10:173-8.
29. Vesselinovitch et al., (1975), *Artherosclerosis*, 19:259-75.
30. Kramsch et al., (1975), *Fed. Proc.*, 34:235-9.
31. Kritchevsky et al., (1986), *J. Atheroscler. Res.*, 8:755-61.
32. U.S. Pat. No. 3,737,433—Mohler et al. (1973)
33. Aviato et al., (1964), *Arch. Int. Pharmacodyn. Ther.*, 27:1932-9.
34. U.S. Pat. No. 4,189,469—Gleixner et al. (1980)
35. Cicardo, V. H. (1980), *Medicina B. Aires*, 40:423-7.
36. Ehrly et al., (1982), *ICRS Med. Sci.*, 10:401-2.
37. Saterwachin et al., (1978), *Pharmatherapeuticia*, 2:109-16.
38. Takamatsu S. (1978), *Third General Meeting Japan Society Stroke Akita*, pp. 33-7.
39. Lowry et al. (1972) Academic Press, Inc., New York; 146-218.
40. Krebs et al., (1970), *J. Biochem.*, 118:635-44.
41. Jarret et al., (1977), *Curr. Med. Res. Opin.*, 4:497-502.
42. Bessler et al., (1986), *J. Leukocyte Biol.*, 40:747-54.
43. Report of the Working Group on Atherosclerosis of the National Heart, Lung, and Blood Pressure Institute, NIH Publication No. 81-2084, Vol. 1 (1984).
44. Lowry et al., (1951), *J. Biol. Chem.*, 193:265.
45. Kaminsky et al., (1982), *Corp. Biochem. Ciochen. Physiol.*, 73:597-63.
46. Chalvardjian et al., (1970), *Anal. Biochem.*, 36:225-36.
47. Dettelbach t al., (1985), *J. Clin. Pharmacol.*, 25:8-26.
48. Nelemans, F. A., (1972), *Arzneim.—For Sch (Drug Res.)*, 22(8):1410-13.
49. Zeller et al., (1966), *Klin Wschr.*, 44:1022-8.
50. Chaub et al., (1970), *Munch. Med. Wschr.*, 112:1265.
51. Aviado, D. M., "Pharmacology of New Vasodilator Drugs" Scriabine A, Sweet CS (eds): *In: New Antihypertensive Drugs*, New York Spetrum Publications Inc., (1976), pp. 505-25.
52. Ehrly et al., (1976), *Microcirculation*, 1:165-71.
53. Anitschow, N. N., (1967), Arteriosclerosis, pp. 21-44.
54. Arvan et al., (1986), *Ann. Clin. Lab. Sci.*, 15(3):252-9.
55. Cavallo et al., (1986), *Acta Endocrinol.*, (Copenh), 112(3):377-82.
56. Scharschmidt et al., (1971)
57. Porikos et al., (1983), *Am. J. Med.*, 75(4):624-30.
58. Ottmar et al., (1989), *Gastro Intest. Radiol.*, 14(1):55-8.

What is claimed is:

1. A method for reversing arterial plaque deposits comprising:

identifying a patient having arterial plaque deposits;

administering to the patient a plaque deposit reversing regimen of a methylxanthine compound having the formula:

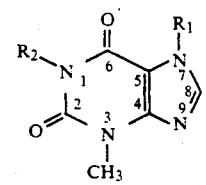

and;

continuing administration of the methylxanthine compound until there is a reversal of the arterial plaque deposit;

wherein $R_1$ is hydrogen or methyl and wherein $R_2$ is hydrogen, a ketone or an alkyl having between 1 and 10 carbon atoms; and wherein $R_2$ is not hydrogen when $R_1$ is hydrogen.

2. A method for reversing plaque deposits of atheromatous lesions, comprising:

identifying a patient with an atheromatous lesions;

administering to the identified patient a plaque deposit revesing regiment of a methylxanthine compound having the formula:

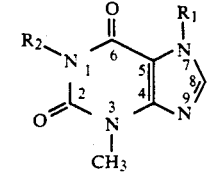

and;

continuing daily administration of the methylxanthine compound until there is a refersal of the plaque deposite of the atheromatous lesion, wherein $R_1$ is hydrogen or methyl and wherein $R_2$ is hydrogen, a ketone or an alkyl having between 1 and 10 carbon atoms, and wherein $R_2$ is not hydrogen when $R_1$ is hydrogen.

3. A method for reversing fatty deposits of fatty liver tissue damage in a patient comprising:

identifying a patient with fatty deposits of a compromised liver condition;

administering to the identified patient a pharmacologically acceptable regimen of a methylxanthine compound having the formula:

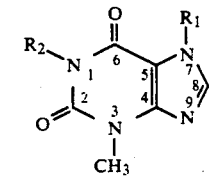

and;

continuing administration of the methylxanthine compound until there is a reversal of the fatty deposits of the liver tissue damage:
wherein $R_1$ is hydrogen or methyl and wherein $R_2$ is hydrogen, a ketone or an alkyl having between 1 and 10 carbon atoms, and
wherein $R_2$ is not hydrogen when $R_1$ is hydrogen.

4. The method of claim 1, 2 or 3, wherein the compound is further defined as comprising a methyl group at $R_1$ and a ketone at $R_2$.

5. The method of claim 4, wherein $R_2$ is a ketone, and wherein the keto group is separated from the xanthine nucleus by 4 carbon atoms.

6. The method of claim 4, wherein $R_2$ is a ketone further defined as 5-ketone.

7. The method of claim 1, 2 or 3 wherein the methylxanthine compound is pentoxifylline or a bioactive equivalent methylxanthine derivative thereof having the structure:

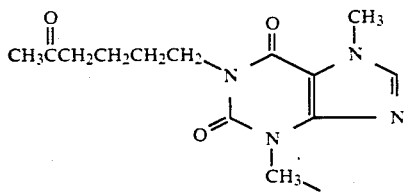

wherein $R_1$ is methyl and wherein $R_2$ is hydrogen, a ketone or an alkyl having between 1 and 20 carbon atoms.

8. The method of claim 7, wherein pentoxifylline is administered to a human patient at a dose of about 1200 mg/day for between 30-90 days.

9. The method of claim 8, wherein pentoxifylline is administered in three separate doses of about 400 mg each.

10. The method of claim 9, wherein the 400 mg dose is in tablet or capsule form.

11. A method for reversing plaque deposits comprising:
identifying a patient having arterial plaque deposits;
administering to the identified patient a arteriosclerotic plaque reversing regiment of a pharmacologically acceptable methylxanthine compound comprising pentoxifylline or a bioactive-equivaeltn methylxanthine derivative thereof; and
continuing administration of the methylxanthine compound until there is a decrease in the arterial plaque deposits.

12. A method for reversing plaque deposits of atheromatous lesions comprising:
identifying a patient with an atheromatous lesion;
administering to the identified patient a plaque deposit-reversing regiment of a methylxanthine compound comprising pentoxifylline or a bioactive-equivalent derivative thereof; and
continuing administration of the methylxanthine compound until there is a reversal of the plaque deposits of the atheromatous lesions.

13. A method for clearing ethanol induced liver tissue damage comprising:
identifying a patient having an ethanol-induced compromised liver condition;
administering to the identified patient a pharmacologically acceptable regiment of a therapeutic agent comprising a pentoxifylline methylxanthine compound or a compound of which pentoxifylline is a metabolite; and
continuing administration of the therapeutic agent until an improverment of the liver tissue damage is indicated.

14. The method of claim 13, wherein identifying a patient having a compromised liver condition comprises identifying a patient with physiologically elevated levels of conjugated bilirubin or transaminase.

15. The method of claim 13, wherein an improvement of liver tissue damage is indicated when a patient's blood toxin level reaches physiologically acceptable levels.

16. The method of claim 13, wherein the compound of which pentoxifylline is a metabolite is 1-[5-hydroxyhexyl]-3,7-dimethylxanthine or 1-[3-carboxypropyl]-3,7-dimethylxanthine.

17. The method of claim 14, wherein an improvement of liver tissue damage is indicated where a physiologically acceptable patient's blood level of conjugated bilirubin is between 0.3 and 1.1 mg/dl.

18. The method of claim 14, wherein an improvement of liver tissue damage is indicated where a patient's serum level of aspartate aminotransferase is between 15 and 40 units aspartate aminotransferase.

19. The method of claim 14, wherein a physiologically elevated level of conjugated bilirubin is a conjugated bilirubin level greater than 1.5 mg/dl.

20. The method of claim 14, wherein a physiologically elevated level of transaminase is identified in serum levels of greater than 50 units aspartate aminotransferase.

* * * * *

UNITED STATES PATENT AND TRADEMARK OFFICE
CERTIFICATE OF CORRECTION

PATENT NO. : 5,112,827

DATED : May 12, 1992

INVENTOR(S) : J. Palmer Saunders, et al.

It is certified that error appears in the above-identified patent and that said Letters Patent is hereby corrected as shown below:

At claim 2, line 32, column 28, delete "revesing regiment" and replace it with --reversing regimen--.

At claim 2, line 46, column 28, delete "refersal" and replace it with --reversal--.

At claim 2, line 47, column 28, delete "deposite" and replace it with --deposit--.

At claim 6, line 17, column 29, delete "ketone" and replace it with --hexone--.

At claim 11, line 49, column 29, delete "regiment" and replace it with --regimen--.

At claim 11, line 51, column 29, delete "equivaeltn" and replace it with --equivalent--.

At claim 12, line 8, column 30, delete "regiment" and replace it with --regimen--.

At claim 13, line 19, column 30, delete "regiment" and replace it with --regimen--.

UNITED STATES PATENT AND TRADEMARK OFFICE
CERTIFICATE OF CORRECTION

PATENT NO.   : 5,112,827
DATED        : May 12, 1992
INVENTOR(S)  : J. Palmer Saunders, et al.

It is certified that error appears in the above-identified patent and that said Letters Patent is hereby corrected as shown below:

Claim 13, line 24, column 30, delete "improverment" and insert--improvement--

Signed and Sealed this

Seventeenth Day of August, 1993

Attest:

BRUCE LEHMAN

Attesting Officer          Commissioner of Patents and Trademarks